(12) United States Patent
Ferrario et al.

(10) Patent No.: US 12,365,739 B2
(45) Date of Patent: Jul. 22, 2025

(54) MONOCLONAL ANTIBODIES TO ANGIOTENSIN-(1-12), COMPOSITIONS INCLUDING THE SAME, AND METHODS OF USE THEREOF

(71) Applicant: Wake Forest University Health Sciences, Winston-Salem, NC (US)

(72) Inventors: Carlos M. Ferrario, Wilmington, NC (US); Sarfaraz Ahmad, Winston-Salem, NC (US); Jasmina Varagic, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 17/702,890

(22) Filed: Mar. 24, 2022

(65) Prior Publication Data

US 2022/0306756 A1    Sep. 29, 2022

Related U.S. Application Data

(60) Provisional application No. 63/165,381, filed on Mar. 24, 2021.

(51) Int. Cl.
*C07K 16/28* (2006.01)
*A61K 39/00* (2006.01)

(52) U.S. Cl.
CPC .... *C07K 16/2869* (2013.01); *A61K 2039/505* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,474,893 A | 10/1984 | Reading | |
| 4,676,980 A | 6/1987 | Segal et al. | |
| 4,816,567 A | 3/1989 | Cabilly et al. | |
| 7,186,809 B2 * | 3/2007 | Pluenneke | C07K 14/7155 530/389.1 |
| 10,035,853 B2 * | 7/2018 | Arathoon | C07K 16/2896 |

OTHER PUBLICATIONS

Ahmad et al. "Angiotensin-(1-12): A Chymase-Mediated Cellular Angiotensin II Substrate" Current Hypertension Reports, 16(5):429 (2014).
Ahmad et al. "Chymase Mediates Angiotensin-(1-12) Metabolism in Normal Human Hearts" Journal of the American Society of Hypertension, 7(2):128-136 (2013).
Ahmad et al. "Chymase-Dependent Generation of Angiotensin II from Angiotensin-(1-12) in Human Atrial Tissue" PLoS One, 6(12):e28501 (2011).
Ahmad et al. "Mast cell peptidases (carboxypeptidase a and chymase)-mediated hydrolysis of human angiotensin-(1-12) substrate" Biochemical and Biophysical Research Communications, 518(4):651-656 (2019).
Ahmad et al. "Primacy of cardiac chymase over angiotensin converting enzyme as an angiotensin-(1-12) metabolizing enzyme" Biochemical and Biophysical Research Communications, 478(2):559-564 (2016).
Ali et al. "The Management of Hypertension in 2018: What Should the Targets Be?" Current Hypertension Reports, 21(41):1-4 (2019).
Arnold et al. "Angiotensin-(1-12) requires angiotensin converting enzyme and AT1 receptors for cardiovascular actions within the solitary tract nucleus" American Journal of Physiology—Heart and Circulatory Physiology, 299:H763-H771 (2010).
Balyasnikova et al. "Monoclonal Antibodies 1G12 and 6A12 to the N-Domain of Human Angiotensin-Converting Enzyme: Fine Epitope Mapping and Antibody-Based Detection of ACE Inhibitors in Human Blood" Journal of Proteome Research, 6(4):1580-1594 (2007).
Carey et al. "Resistant Hypertension: Detection, Evaluation, and Management: A Scientific Statement From the American Heart Association" Hypertension, 72:e53-e90 (2018).
Celerier et al. "Angiotensinogen and Its Cleaved Derivatives Inhibit Angiogenesis" Hypertension, 39(2):224-228 (2002).
Chen et al. "Effectiveness and Safety of a Therapeutic Vaccine Against Angiotensin II Receptor Type 1 in Hypertensive Animals" Hypertension, 61(2):408-416 (2013).
Cole et al. "Human monoclonal antibodies" Molecular and Cellular Biology, 62:109-120 (1984).
Corvol et al. "Inhibition of angiogenesis: A new function for angiotensinogen and des(angiotensin i)angiotensinogen" Current Hypertension Reports, 5:149-154 (2003).
Cote et al. "Generation of human monoclonal antibodies reactive with cellular antigens" Proceedings of the National Academy of Sciences USA, 80(7):2026-2030 (1983).
De Mello et al. "Intracellular angiotensin-(1-12) changes the electrical properties of intact cardiac muscle" Molecular and Cellular Biochemistry, 422:31-40 (2016).
Ding et al. "Vaccination against type 1 angiotensin receptor prevents streptozotocin-induced diabetic nephropathy" Journal of Molecular Medicine (Berlin, Germany), 94(2):207-218 (2016).
Dusing, Rainer "Mega clinical trials which have shaped the RAS intervention clinical practice" Therapeutic Advances in Cardiovascular Disease, 10:133-150 (2016).
Dzau et al. "Antibodies as specific renin inhibitors: Studies with polyclonal and monoclonal antibodies and fab fragments" Clinical and Experimental Hypertension, Part A, 5:1207-1220 (1983).
Ferrario et al. "Activation of the Human Angiotensin-(1-12)-Chymase Pathway in Rats With Human Angiotensinogen Gene Transcripts" Frontiers in Cardiovascular Medicine, 6:163 (2019).
Ferrario et al. "Cardiac angiotensin-(1-12) expression and systemic hypertension in rats expressing the human angiotensinogen gene" American Journal of Physiology—Heart and Circulatory Physiology, 310:H995-H1002 (2016).
Ferrario et al. "Differential regulation of angiotensin-(1-12) in plasma and cardiac tissue in response to bilateral nephrectomy" American Journal of Physiology—Heart and Circulatory Physiology, 296:H1184-H1192 (2009).

(Continued)

*Primary Examiner* — Marianne P Allen
(74) *Attorney, Agent, or Firm* — Myers Bigel, P.A.

(57) ABSTRACT

The present invention relates to monoclonal antibodies to angiotensin-(1-12) as well as compositions comprising the same and methods of using the same.

11 Claims, 7 Drawing Sheets

Specification includes a Sequence Listing.

(56) References Cited

OTHER PUBLICATIONS

Ferrario et al. "Intracrine angiotensin II functions originate from noncanonical pathways in the human heart" American Journal of Physiology—Heart and Circulatory Physiology, 311:H404-H414 (2016).
Ferrario, Carlos M. "New Physiological Concepts of the Renin-Angiotensin System From the Investigation of Precursors and Products of Angiotensin I Metabolism" Hypertension, 55(2):445-452 (2010).
Ganten et al. "Species specificity of renin kinetics in transgenic rats harboring the human renin and angiotensinogen genes" Proceedings of the National Academy of Sciences USA, 89:7806-7810 (1992).
Garay-Gutierrez et al. "Vaccines against components of the renin-angiotensin system" Heart Failure Reviews, pp. 1-16 (2020).
Huang et al. "Dose-related reductions in blood pressure with a rna interference (rnai) therapeutic targeting angiotensinogen in hypertensive patients" Circulation, vol. 142, Abstract 14387 (2020).
Huse et al. "Generation of a Large Combinatorial Library of the Immunoglobulin Repertoire in Phage Lambda" Science, 254(4935):1275-1281 (1989).
Isa et al. "Angiotensin-(1-12) contributes to renin-independent angiotensin II activity in brain" Conference Abstracts—62nd High Blood Pressure Research Conference, Abstract p. 126 (2018).
Isa et al. "Chronic immunoneutralization of brain angiotensin-(1-12) lowers blood pressure in transgenic (mren2)27 hypertensive rats" American Journal of Physiology—Regulatory, Integrative and Comparative Physiology, 297:R111-R115 (2009).
Iyer et al. "Contribution of angiotensin-(1-7) to blood pressure regulation in salt-depleted hypertensive rats" Hypertension, 36(3)::417-422 (2000).
Iyer et al. "Vasodepressor actions of angiotensin-(1-7) unmasked during combined treatment with lisinopril and losartan" Hypertension, 31:699-705 (1998).
Kang et al. "Antibody redesign by chain shuffling from random combinatorial immunoglobulin libraries" Proceedings of the National Academy of Sciences USA, 88:11120-11123 (1991).
Kennedy et al. "Anti-Idiotypic Antibody Vaccine for Type B Viral Hepatitis in Chimpanzees" Science, 232(4747):220-223 (1986).
Kohler et al. "Continuous cultures of fused cells secreting antibody of predefined specificity" Nature, 265:495-497 (1975).
Kozbor et al. "Specific immunoglobulin production and enhanced tumorigenicity following ascites growth of human hybridomas" Journal of Immunological Methods, 81:31-42 (1985).
Kurashiki et al. "Prevention of progression of aortic aneurysm by peptide vaccine against ang ii (angiotensin ii) in a rat model" Hypertension, 76:1879-1888 (2020).
Lee et al. "Antenatal betamethasone increases vascular reactivity to endothelin-1 by upregulation of cd38/cadpr signaling" Journal of Developmental Origins of Health and Disease, 5:56-62 (2014).
Li et al. "Critical role of the chymase/angiotensin-(1-12) axis in modulating cardiomyocyte contractility" International Journal of Cardiology, 264:137-144 (2018).
Li et al. "Reversal of angiotensin-(1-12)-caused positive modulation on left ventricular contractile performance in heart failure: Assessment by pressure-vol. analysis" International Journal of Cardiology, 301:135-141 (2020).
Lin et al. "Preclinical pharmacokinetics, interspecies scaling, and tissue distribution of a humanized monoclonal antibody against vascular endothelial growth factor" Journal of Pharmacology and Experimental Therapeutics, 288:371-378 (1999).
Lobo et al. "Antibody Pharmacokinetics and Pharmacodynamics" Journal of Pharmaceutical Science, 93(11):2645-2668 (2004).
Lu et al. "Angiotensinogen Exerts Effects Independent of Angiotensin II" Arteriosclerosis, Thrombosis, and Vascular Biology, 36:256-265 (2016).
Lu et al. "Development of therapeutic antibodies for the treatment of diseases" Journal of Biomedical Science, 27:1 (2020).
Lu et al. "Structure and functions of angiotensinogen" Hypertension Research, 39:492-500 (2016).
Mak TW, Saunders ME. 7—exploiting antigen-antibody interaction. In: Mak TW, Saunders ME, eds. The immune response. Burlington: Academic Press; 2006:147-177.
McNamara et al. "Monoclonal Idiotope Vaccine Against *Streptococcus pneumoniae* Infection" Science, 220(4680):1325-1326 (1984).
Moniwa et al. "Primacy of angiotensin converting enzyme in angiotensin-(1-12) metabolism" American Journal of Physiology—Heart and Circulatory Physiology, 305:H644-H650 (2013).
Morimoto et al. "Elevated Blood Pressure in Transgenic Mice With Brain-Specific Expression of Human Angiotensinogen Driven by the Glial Fibrillary Acidic Protein Promoter" Circulation Research, 89(4):365-372 (2001).
Morrison et al. "Chimeric human antibody molecules: Mouse antigen-binding domains with human constant region domains" Proceedings of the National Academy of Sciences USA, 81:6851-6855 (1984).
Mullick et al. "Blood Pressure Lowering and Safety Improvements With Liver Angiotensinogen Inhibition in Models of Hypertension and Kidney Injury" Hypertension, 70(3):566-576 (2017).
Nagata et al. "Isolation and identification of proangiotensin-12, a possible component of the renin-angiotensin system" Biochemical and Biophysical Research Communications, 350(4):1026-1031 (2006).
Neuberger et al. "Recombinant antibodies possessing novel effector functions" Nature, 312:604-608 (1984).
Orlandi et al. "Cloning immunoglobulin variable domains for expression by the polymerase chain reaction" Proceedings of the National Academy of Sciences USA, 86(10):3833-3837 (1989).
Ovacik et al. "Tutorial on Monoclonal Antibody Pharmacokinetics and Its Considerations in Early Development" Clinical and Translational Science, 11(6):540-552 (2018).
Percie Du Sert et al. "The ARRIVE guidelines 2.0: Updated guidelines for reporting animal research" PLoS Biology, 18:e3000410 (2020).
Prosser et al. "Cardiac chymase converts rat proAngiotensin-12 (PA12) to angiotensin II: Effects of PA12 upon cardiac haemodynamics" Cardiovascular Research, 82:40-50 (2009).
Prosser et al. "Regional vascular response to ProAngiotensin-12 (PA12) through the rat arterial system" Peptides, 31(8):1540-1545 (2010).
Ravichandran et al. "Antisense-mediated angiotensinogen inhibition slows polycystic kidney disease in mice with a targeted mutation in pkd2" American Journal of Physiology—Renal Physiology, 308(4):F349-F357 (2015).
Reddy et al. "Circulating angiotensin peptides levels in acute respiratory distress syndrome correlate with clinical outcomes: A pilot study" PLoS One, 14(3):e0213096 (2019).
Reilly et al. "Characterization of the functional antagonism and antihypertensive activity displayed by a monoclonal antibody to angiotensin II" Journal of Pharmacology and Experimental Therapeutics, 244:160-165 (1988).
Reyes et al. "Angiotensin-(1-12)/chymase axis modulates cardiomyocyte I-type calcium currents in rats expressing human angiotensinogen" International Journal of Cardiology, 297:104-110 (2019).
Reyes et al. "Novel Cardiac Intracrine Mechanisms Based on Ang-(1-12)/Chymase Axis Require a Revision of Therapeutic Approaches in Human Heart Disease" Current Hypertension Reports, 19:16 (2017).
Sun et al. "Potential Cure for Hypertension? The Effect of Crispr Genome Editing" Circulation, 142, Abstract 15555 (2020).
Takeda et al. "Construction of chimaeric processed immunoglobulin genes containing mouse variable and human constant region sequences" Nature, 314:452-454 (1985).
Trask et al. "Angiotensin-(1-12) is an alternate substrate for angiotensin peptide production in the heart" American Journal of Physiology—Heart and Circulatory Physiology, 294(5):H2242-H2247 (2008).
Uijl et al. "Strong and Sustained Antihypertensive Effect of Small Interfering RNA Targeting Liver Angiotensinogen" Hypertension, 73(6):1249-1257 (2019).

(56) References Cited

OTHER PUBLICATIONS

Walker et al. "Interaction of human IgG chimeric antibodies with the human FcRI and FcRII receptors: requirements for antibody-mediated host cell-target cell interaction" Molecular Immunology, 26:403-411 (1989).

Walker et al. "Pharmacokinetic comparison of a diverse panel of non-targeting human antibodies as matched IgG1 and IgG2 isotypes in rodents and non-human primates" PLoS One, 14:e0217061 (2019).

Winter et al. "Man-made antibodies" Nature, 349:293-299 (1991).

Wu et al. "Antisense oligonucleotides targeting angiotensinogen: insights from animal studies" Bioscience Reports, 39:1-10 (2019).

Wu et al. "Cys18-Cys137 Disulfide Bond in Mouse Angiotensinogen Does Not Affect AngII-Dependent Functions In Vivo" Hypertension, 65(4):800-805 (2015).

Wu et al. "Effects of Renin-Angiotensin Inhibition on ACE2 and TMPRSS2 Expression: Insights into COVID-19" bioRxiv, pp. 1-4 (2020).

Wu et al. "Elevation of plasma angiotensin II level is a potential pathogenesis for the critically ill COVID-19 patients" Critical Care, 24:290 (2020).

Yan et al. "Structural basis for the specificity of renin-mediated angiotensinogen cleavage" Journal of Biological Chemistry, 294(7):2353-2364 (2019).

Ye et al. "Angiotensinogen and Megalin Interactions Contribute to Atherosclerosis—Brief Report" Arteriosclerosis, Thrombosis, and Vascular Biology, 39(2):150-155 (2019).

\* cited by examiner

MONOCLONAL ANTIBODIES TO ANGIOTENSIN-(1-12), COMPOSITIONS INCLUDING THE SAME, AND METHODS OF USE THEREOF

PRIORITY STATEMENT

This application claims the benefit, under 35 U.S.C. § 119(e), of U.S. Provisional Application Ser. No. 63/165,381, filed Mar. 24, 2021, the entire contents of which are incorporated by reference herein.

STATEMENT OF GOVERNMENT SUPPORT

This invention was made with government support under HL051952 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 9151-258_12212023_ST25.txt, 11,081 bytes in size, generated on Dec. 21, 2023 and filed electronically, is provided in lieu of a paper copy. This Sequence Listing is hereby incorporated herein by reference into the specification for its disclosures.

FIELD OF THE INVENTION

The present invention relates to monoclonal antibodies to angiotensin-(1-12) as well as compositions comprising the same and methods of using the same.

BACKGROUND OF THE INVENTION

It is universally accepted that hepatic and tissue-borne angiotensinogen (AGT) is the sole substrate in which renin initiates the biochemical cascade leading to the sequential formation of angiotensin I (Ang I), and its conversion by ACE into Ang II in the circulation and even in the tissues. The classical biochemical pathways for the formation of biologically active angiotensin II (Ang II) peptides continues to undergo significant revision as alternate renin-independent mechanisms are uncovered, both in humans and rodents[1, 2]. The discovery of angiotensin-(1-12) [Ang-(1-12)] as an angiotensin II (Ang II)-forming substrate expands our understanding of the role played by the renin angiotensin system (RAS) in the pathogenesis of cardiovascular diseases.[3, 4] This alternate substrate forms Ang II primarily through the hydrolytic activity of ACE in the circulation and chymase in the rodent and human heart.[5-8] Given efficacy limitations of current medications, low adherence to therapy, physician inertia, and side effects,[9-12] alternate therapies are recently proposed based on the inhibition of the hepatic AGT protein by means of gene silencing with small interfering RNA (siRNA)[13, 14] or antisense RNA.[14, 15] The fact that these approaches depend upon the complete long-term inhibition of the AGT protein is a concern as emerging data suggest that des-(Arg¹)AGT has functions beyond those of serving as a substrate for the formation of angiotensin I (Ang I).[16-19]

The present invention overcomes shortcomings in the art by providing monoclonal antibodies to angiotensin-(1-12) as well as compositions comprising the same and methods of using the same.

SUMMARY OF THE INVENTION

One aspect of the present invention relates to a monoclonal antibody or a fragment thereof, wherein the monoclonal antibody or the fragment thereof binds to human angiotensin-(1-12).

Another aspect of the present invention relates to a monoclonal antibody or a fragment thereof, wherein the monoclonal antibody or the fragment thereof comprises a heavy chain variable region comprising a VDJ junction region comprising an amino acid sequence having at least about 70%, 75%, 80%, 85%, 90%, 95%, or 100% sequence identity to SEQ ID NO:1.

Another aspect of the present invention relates to a monoclonal antibody or a fragment thereof, wherein the monoclonal antibody or the fragment thereof comprises a light chain variable region comprising a VDJ junction region comprising an amino acid sequence having at least about 70%, 75%, 80%, 85%, 90%, 95%, or 100% sequence identity to SEQ ID NO:2.

In some embodiments, the monoclonal antibodies or fragments thereof of the present invention bind to human angiotensin-(1-12).

Another aspect of the present invention relates to pharmaceutical compositions comprising the monoclonal antibody or the fragment thereof of the present invention and a pharmaceutically acceptable carrier.

Another aspect of the present invention relates to isolated nucleic acid molecules encoding the monoclonal antibody or the fragment thereof of the present invention.

Another aspect of the present invention relates to hybridoma cells comprising the monoclonal antibody or the fragment thereof and/or the isolated nucleic acid molecule of the present invention.

Also provided herein are kits comprising the monoclonal antibody or the fragment thereof, pharmaceutical compositions, isolated nucleic acid molecules and/or hybridoma cells of the present invention, and instructions for use of the kit.

Another aspect of the present invention relates to a method of reducing, inhibiting, and/or blocking one or more angiotensin II pathological mechanisms and/or actions, the method comprising contacting angiotensin-(1-12) and the monoclonal antibody or the fragment thereof of the present invention, thereby reducing, inhibiting, and/or blocking one or more Ang II pathological mechanisms and/or actions Another aspect of the present invention relates to a method of treating and/or preventing a disorder in a subject, the method comprising administering to the subject a therapeutically effective amount of the monoclonal antibody or the fragment thereof of the present invention, thereby treating and/or preventing the disorder in the subject In some embodiments, the monoclonal antibody or the fragment thereof may reduce or inhibit enzymatic cleavage of angiotensin-(1-12) to form angiotensin II.

Additionally provided herein are antibodies, compositions, articles, systems, and/or methods as described and/or shown herein.

DETAILED DESCRIPTION

Figure 1:
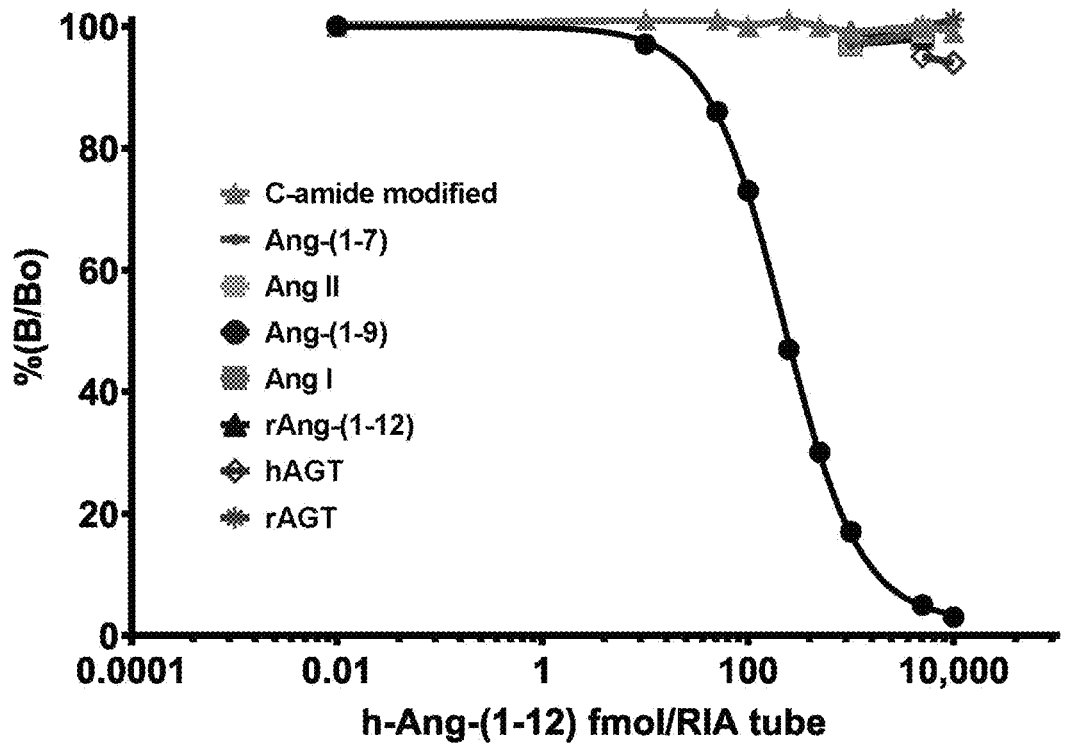
FIG. 1 shows a data graph regarding the specificity of Protein L purified mAb (Clone #14B3) for the h-Ang-(1-12) sequence [filled black circle] and cross-reactivity [with various angiotensin peptides (1,000 and 5,000 fmol) or AGT protein (5,000 and 10,000 fmol)] as examined by RIA.

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measurable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to 15 is disclosed, then 11, 12, 13, and 14 are also disclosed.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "enhance," "enhancing," "improve" and "improving" (and grammatical variations thereof) describe an elevation of at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more such as compared to another measurable property or quantity (e.g., a control value).

As used herein, the terms "reduce," "reduced," "reducing," "reduction," "diminish," and "decrease" (and grammatical variations thereof), describe, for example, a decrease of at least about 5%, 10%, 15%, 20%, 25%, 30%, 35%, 40%, 45%, 50%, 55%, 60%, 65%, 70%, 75%, 80%, 85%, 90%, 95%, 97%, 98%, 99%, or 100% such as compared to another measurable property or quantity (e.g., a control value). In some embodiments, the reduction can result in no or essentially no (i.e., an insignificant amount, e.g., less than about 10% or even 5%) detectable activity or amount.

As used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "nucleic acid construct," "recombinant nucleic acid," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. A "5' region" as used herein can mean the region of a polynucleotide that is nearest the 5' end of the polynucleotide. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end of the polynucleotide. Thus, for example, an element in the 3' region of a polynucleotide can be located anywhere from the first nucleotide located at the 3' end of the polynucleotide to the nucleotide located halfway through the polynucleotide.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence as compared to a reference polypeptide.

As used herein, the phrase "substantially identical," or "substantial identity" in the context of two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% nucleotide or amino acid residue identity, when compared and aligned for maximum correspondence, as measured using one of the following sequence comparison algorithms or by visual inspection. In some embodiments of the invention, the substantial identity exists over a region of consecutive nucleotides of a nucleotide sequence of the invention that is about 10 nucleotides to about 20 nucleotides, about 10 nucleotides to about 25 nucleotides, about 10 nucleotides to about 30 nucleotides, about 15 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, or more nucleotides in length, and any range therein, up to the full length of the sequence. In some embodiments, the nucleotide sequences can be substantially identical over at least about 20 nucleotides (e.g., about 20, 21, 22, 23, 24, 25, 26, 27, 28, 29, 30, 31, 32, 33, 34, 35, 36, 37, 38, 39, 40 nucleotides). In some embodiments, a substantially identical nucleotide or protein sequence performs substantially the same function as the nucleotide (or encoded protein sequence) to which it is substantially identical.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, CA). An "identity fraction" for aligned segments of a test sequence and a reference sequence is the number of identical components which are shared by the two aligned sequences divided by the total number of components in the reference sequence segment, e.g., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Two nucleotide sequences may also be considered substantially complementary when the two sequences hybridize to each other under stringent conditions. In some representative embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, N.Y. (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

As used herein, the term "chimera," "chimeric," and/or "fusion protein" refer to an amino acid sequence (e.g., polypeptide) generated non-naturally by deliberate human design comprising, among other components, an amino acid sequence of a protein of interest and/or a modified variant and/or active fragment thereof (a "backbone"), wherein the protein of interest comprises modifications (e.g., substitutions such as singular residues and/or contiguous regions of amino acid residues) from different wild type reference sequences (chimera), optionally linked to other amino acid segments (fusion protein). The different components of the designed protein may provide differing and/or combinatorial function. Structural and functional components of the designed protein may be incorporated from differing and/or a plurality of source material. The designed protein may be delivered exogenously to a subject, wherein it would be exogenous in comparison to a corresponding endogenous protein.

As used herein with respect to nucleic acids, the term "operably linked" refers to a functional linkage between two or more nucleic acids. For example, a promoter sequence may be described as being "operably linked" to a heterologous nucleic acid sequence because the promoter sequence initiates and/or mediates transcription of the heterologous nucleic acid sequence. In some embodiments, the operably linked nucleic acid sequences are contiguous and/or are in the same reading frame.

A "recombinant" nucleic acid, polynucleotide or nucleotide sequence is one produced by genetic engineering techniques.

A "recombinant" polypeptide is produced from a recombinant nucleic acid, polypeptide or nucleotide sequence.

As used herein, by "isolate" or "purify" (or grammatical equivalents) a compound (e.g., an antibody), it is meant that the compound is at least partially separated from at least some of the other components in the starting material.

As used herein, an "isolated" polynucleotide (e.g., an "isolated nucleic acid" or an "isolated nucleotide sequence") means a polynucleotide at least partially separated from at least some of the other components of the naturally occurring organism or virus, for example, the cell or viral structural components or other polypeptides or nucleic acids commonly found associated with the polynucleotide. Optionally, but not necessarily, the "isolated" polynucleotide is present at a greater concentration (i.e., is enriched) as compared with the starting material (e.g., at least about a two-fold, three-fold, four-fold, ten-fold, twenty-fold, fifty-fold, one-hundred-fold, five-hundred-fold, one thousand-fold, ten thousand-fold or greater concentration). In representative embodiments, the isolated polynucleotide is at least about 1%, 5%, 10%, 20%, 30%, 40%, 50%, 60%, 70%, 80%, 90%, 95% or more pure.

An "isolated" polypeptide means a polypeptide that is at least partially separated from at least some of the other components of the naturally occurring organism or virus, for example, the cell or viral structural components or other polypeptides or nucleic acids commonly found associated with the polypeptide. Optionally, but not necessarily, the "isolated" polypeptide is present at a greater concentration (i.e., is enriched) as compared with the starting material (e.g., at least about a two-fold, three-fold, four-fold, ten-fold, twenty-fold, fifty-fold, one-hundred-fold, five-hundred-fold, one thousand-fold, ten thousand-fold or greater concentration). In representative embodiments, the isolated polypeptide is at least about 1%, 5%, 10%, 20%, 30%, 40%, 50%, 60%, 70%, 80%, 90%, 95% or more pure.

Furthermore, an "isolated" cell is a cell that has been partially or completely separated from other components with which it is normally associated in nature. For example, an isolated cell can be a cell in culture medium and/or a cell in a pharmaceutically acceptable carrier.

The term "endogenous" refers to a component naturally found in an environment, i.e., a gene, nucleic acid, miRNA, protein (e.g., antibody), cell, or other natural component expressed in the subject, as distinguished from an introduced component, i.e., an "exogenous" component.

As used herein, the term "heterologous" refers to a nucleotide/polypeptide that originates from a foreign species, or, if from the same species, is substantially modified from its native form in composition and/or genomic locus by deliberate human intervention.

As used herein with respect to nucleic acids, the term "fragment" refers to a nucleic acid that is reduced in length relative to a reference nucleic acid and that comprises, consists essentially of and/or consists of a nucleotide sequence of contiguous nucleotides identical or almost identical (e.g., 90%, 91%, 92%, 93%, 94%, 95%, 96%, 97%, 98%, 99% identical) to a corresponding portion of the reference nucleic acid. Such a nucleic acid fragment may be, where appropriate, included in a larger polynucleotide of which it is a constituent. In some embodiments, the nucleic acid fragment comprises, consists essentially of or consists of at least about 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 300, 350, 400, 450, 500, or more consecutive nucleotides. In some embodiments, the nucleic acid fragment comprises, consists essentially of or consists of less than about 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 300, 350, 400, 450 or 500 consecutive nucleotides.

As used herein with respect to polypeptides, the term "fragment" refers to a polypeptide that is reduced in length relative to a reference polypeptide and that comprises, consists essentially of and/or consists of an amino acid sequence of contiguous amino acids identical or almost identical (e.g., 90%, 91%, 92%, 93%, 94%, 95%, 96%, 97%, 98%, 99% identical) to a corresponding portion of the reference polypeptide. Such a polypeptide fragment may be, where appropriate, included in a larger polypeptide of which it is a constituent. In some embodiments, the polypeptide fragment comprises, consists essentially of or consists of at least about 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 300, 350, 400, 450, 500, or more consecutive amino acids. In some embodiments, the polypeptide fragment comprises, consists essentially of or consists of less than about 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 300, 350, 400, 450 or 500 consecutive amino acids.

As used herein with respect to nucleic acids, the term "functional fragment" or "active fragment" refers to nucleic acid that encodes a functional fragment of a polypeptide.

As used herein with respect to polypeptides, the term "functional fragment" or "active fragment" refers to polypeptide fragment that retains at least about 20%, 25%, 30%, 35%, 40%, 45%, 50%, 55%, 60%, 65%, 70%, 75%, 80%, 85%, 90%, 95%, 96%, 97%, 98%, 99%, 99.5% or more of at least one biological activity of the full-length polypeptide (e.g., the ability to up- or down-regulate gene expression). In some embodiments, the functional fragment actually has a higher level of at least one biological activity of the full-length polypeptide.

As used herein, the term "modified," as applied to a polynucleotide or polypeptide sequence, refers to a sequence that differs from a wild-type sequence due to one or more deletions, additions, substitutions, or any combination thereof. Modified sequences may also be referred to as "modified variant(s)."

The terms "immunogen" and "antigen" are used interchangeably herein and mean any compound (including polypeptides) to which a cellular and/or humoral immune response can be directed. A molecule capable of antibody and/or immune response stimulation may be referred to as antigenic/immunogenic, and can be said to have the ability of antigenicity/immunogenicity. The binding site for an antibody within an antigen and/or immunogen may be referred to as an epitope (e.g., an antigenic epitope).

The term "administering" or "administration" of a composition of the present invention to a subject includes any route of introducing or delivering to a subject a compound to perform its intended function (e.g., for use as a therapeutic). Administration includes self-administration and the administration by another.

"Pharmaceutically acceptable" as used herein means that the compound, carrier, or composition is suitable for administration to a subject to achieve a treatment described herein, without unduly deleterious side effects in light of the severity of the disease and necessity of the treatment.

As used herein, the term "therapeutically effective amount" refers to an amount of a monoclonal antibody or a fragment thereof and/or a composition of the present invention that elicits a therapeutically useful response in a subject. Those skilled in the art will appreciate that the therapeutic effects need not be complete or curative, as long as some benefit is provided to the subject.

"Treat," "treating" or "treatment of" (and grammatical variations thereof) as used herein refer to any type of treatment that imparts a benefit to a subject and may mean that the severity of the subject's condition is reduced, at least partially improved or ameliorated and/or that some alleviation, mitigation or decrease in at least one clinical symptom associated with angiotensin-(1-12) and/or angiotensin II is achieved and/or there is a delay in the progression of the symptom. In some embodiments, the severity of a symptom associated with angiotensin-(1-12), angiotensin II, and/or cardiovascular disease may be reduced in a subject compared to the severity of the symptom in the absence of a method of the present invention.

A "treatment effective" amount as used herein is an amount that is sufficient to treat (as defined herein) a subject. Those skilled in the art will appreciate that the therapeutic effects need not be complete or curative, as long as some benefit is provided to the subject. In some embodiments, a treatment effective amount may be achieved by administering a composition of the present invention.

The terms "prevent," "preventing" and "prevention" (and grammatical variations thereof) refer to avoidance, reduction and/or delay of the onset of a symptom associated with angiotensin-(1-12) and/or angiotensin II and/or a reduction in the severity of the onset of symptom associated with angiotensin-(1-12) and/or angiotensin II relative to what would occur in the absence of a method of the present invention. The prevention can be complete, e.g., the total absence of the symptom. The prevention can also be partial, such that the occurrence of the symptom in the subject and/or the severity of onset is less than what would occur in the absence of a method of the present invention.

A "prevention effective" amount as used herein is an amount that is sufficient to prevent (as defined herein) a symptom associated with angiotensin-(1-12) and/or angiotensin II in a subject. Those skilled in the art will appreciate that the level of prevention need not be complete, as long as some benefit is provided to the subject. In some embodiments, a prevention effective amount may be achieved by administering a composition of the present invention.

The present invention finds use in both veterinary and medical applications. Subjects suitable to be treated with a method of the present invention include, but are not limited to, mammalian subjects. Mammals of the present invention include, but are not limited to, canines, felines, bovines, caprines, equines, ovines, porcines, rodents (e.g. rats and mice), lagomorphs, primates (e.g., simians and humans), non-human primates (e.g., monkeys, baboons, chimpanzees, gorillas), and the like, and mammals in utero. Any mammalian subject in need of being treated according to the present invention is suitable. Human subjects of all genders and at any stage of development (i.e., neonate, infant, juvenile, adolescent, adult) may be treated according to the present invention. In some embodiments of the present invention, the subject is a mammal and in certain embodiments the subject is a human. Human subjects include both males and females of all ages including fetal, neonatal, infant, juvenile, adolescent, adult, and geriatric subjects as well as pregnant subjects. In particular embodiments of the present invention, the subject is a human adolescent and/or adult.

A method of the present invention may also be carried out on animal subjects, particularly mammalian subjects such as mice, rats, dogs, cats, livestock and horses for veterinary purposes, and/or for drug screening and drug development purposes.

A "sample" or "biological sample" of this invention can be any biological material, such as a biological fluid, an extract from a cell, an extracellular matrix isolated from a cell, a cell (in solution or bound to a solid support), a tissue, a tissue homogenate, and the like as are well known in the art.

In some embodiments, the subject is "in need of" or "in need thereof" a method of the present invention, for example, the subject has findings typically associated with angiotensin-(1-12) and/or angiotensin II.

The term "antibody" or "antibodies" as used herein refers to all types of immunoglobulins, including IgG, IgM, IgA, IgD, and IgE. The antibody can be monoclonal or polyclonal and can be of any species of origin, including, for example, mouse, rat, rabbit, horse, goat, sheep or human, or can be a chimeric or humanized antibody. See, e.g., Walker et al., Molec. Immunol. 26:403-11 (1989). The antibodies can be recombinant monoclonal antibodies produced according to the methods disclosed in U.S. Pat. No. 4,474,893 or 4,816, 567. The antibodies can also be chemically constructed according to the method disclosed in U.S. Pat. No. 4,676, 980. The antibody can further be a single chain antibody or bispecific antibody. The antibody can also be humanized for administration to a human subject.

Non-limiting examples of an antibody or fragment thereof of the present invention include a monoclonal antibody or fragment thereof, a chimeric antibody or fragment thereof, a CDR-grafted antibody or fragment thereof, a humanized antibody or fragment thereof, an Fc, a Fab, a Fab', a F(ab')2, a Fv, a disulfide linked Fv, a single chain antibody (scFv), a single domain antibody (dAb), a diabody, a multispecific antibody (e.g., a bispecific antibody) or fragment thereof, an anti-idiotypic antibody or fragment thereof, a bifunctional hybrid antibody or fragment thereof, a functionally active epitope-binding antibody fragment, an affibody, a nanobody, and any combination thereof. Antibody fragments included within the scope of the present invention include, for example, Fab, F(ab')2, and Fc fragments, and the corresponding fragments obtained from antibodies other than IgG. Such fragments can be produced by known techniques. For example, F(ab')2 fragments can be produced by pepsin digestion of the antibody molecule, and Fab fragments can be generated by reducing the disulfide bridges of the F(ab')2 fragments. Alternatively, Fab expression libraries can be constructed to allow rapid and easy identification of monoclonal Fab fragments with the desired specificity (Huse et al., (1989) Science 254:1275-1281).

Monoclonal antibodies can be produced in a hybridoma cell line according to the technique of Kohler and Milstein, (1975) Nature 265:495-97. For example, a solution containing the appropriate antigen can be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in bacterial cell such as *E. coli* by recombinant techniques known to those skilled in the art. See, e.g., W. Huse, (1989) Science 246:1275-81.

Antibodies can also be obtained by phage display techniques known in the art or by immunizing a heterologous host with a cell containing an epitope of interest.

Compositions

Angiotensin (Ang) (1-12) is an endogenous Ang II-forming substrate that contributes to the maintenance of arterial pressure. This invention is based, in part, on the discovery by the inventors of the present invention which found that immunoneutralization of Ang-(1-12) by means of a selective monoclonal antibody directed against the human Ang-(1-12) sequence blocks the vasoconstrictor activity of this Ang II-generating substrate in the circulation of both SD and transgenic hypertensive rats expressing the human AGT gene and isolated carotid artery strips from both strains. While not wishing to be bound to theory, these results suggest that this alternate Ang II-forming substrate is a functional mechanism contributing to blood pressure control. As such, the antibodies disclosed herein may be suitable candidates for long-term control of blood pressure alone or in combination with other antihypertensive medications.

Accordingly, one aspect of the present invention provides a monoclonal antibody or a fragment thereof, wherein the monoclonal antibody or the fragment thereof binds to human angiotensin-(1-12).

In some embodiments, the monoclonal antibody or the fragment thereof of the present invention (e.g., that binds to human angiotensin-(1-12)) may comprise a heavy chain variable region comprising a VDJ junction region comprising an amino acid sequence having at least about 70% (e.g., about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%) sequence identity to SEQ ID NO:1.

```
                                       SEQ ID NO: 1
CARGSYYFDYW.
```

In some embodiments, the monoclonal antibody or the fragment thereof of the present invention (e.g., that binds to human angiotensin-(1-12)) may comprise a light chain variable region comprising a VDJ junction region comprising an amino acid sequence having at least about 70% (e.g., about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%) sequence identity to SEQ ID NO:2.

```
                                       SEQ ID NO: 2
CKQSYNLRTF.
```

Another aspect of the present invention provides a monoclonal antibody or a fragment thereof, wherein the monoclonal antibody or the fragment thereof comprises a heavy chain variable region comprising a VDJ junction region comprising an amino acid sequence having at least about 70% (e.g., about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%) sequence identity to SEQ ID NO:1.

In some embodiments, the monoclonal antibody or the fragment thereof of the present invention (e.g., the monoclonal antibody or the fragment thereof which comprises a heavy chain variable region comprising a VDJ junction region comprising an amino acid sequence having at least about 70% sequence identity to SEQ ID NO:1) binds to human angiotensin-(1-12).

In some embodiments, the monoclonal antibody or the fragment thereof of the present invention (e.g., the monoclonal antibody or the fragment thereof which comprises a heavy chain variable region comprising a VDJ junction region comprising an amino acid sequence having at least about 70% sequence identity to SEQ ID NO:1), further comprises a light chain variable region comprising a VDJ junction region comprising an amino acid sequence having at least about 70% (e.g., about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%) sequence identity to SEQ ID NO:2.

Another aspect of the present invention provides a monoclonal antibody or a fragment thereof, wherein the monoclonal antibody or the fragment thereof comprises a light chain variable region comprising a VDJ junction region comprising an amino acid sequence having at least about 70% (e.g., about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%) sequence identity to SEQ ID NO:2.

In some embodiments, monoclonal antibody or the fragment thereof (e.g., the monoclonal antibody or the fragment thereof which comprises a light chain variable region comprising a VDJ junction region comprising an amino acid sequence having at least about 70% sequence identity to SEQ ID NO:2) binds to human angiotensin-(1-12).

In some embodiments, the monoclonal antibody or the fragment thereof of the present invention (e.g., the monoclonal antibody or the fragment thereof which comprises a light chain variable region comprising a VDJ junction region comprising an amino acid sequence having at least about 70% sequence identity to SEQ ID NO:2), further comprises a heavy chain variable region comprising a VDJ junction region comprising an amino acid sequence having at least about 70% (e.g., about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%) sequence identity to SEQ ID NO:1.

In some embodiments, a monoclonal antibody or fragment thereof of the present invention may further comprise a light chain (LC) complementarity determining region (LC CDR) having a sequence of SEQ ID NO:3 (LC CDR1), SEQ ID NO:4 (LC CDR2), or SEQ ID NO:5 (LC CDR3).

In some embodiments, a monoclonal antibody or the fragment thereof of the present invention may further comprise two or more LC CDRs, e.g., two LC CDRs, three LC CDRs, or more. In some embodiments, a monoclonal antibody or the fragment thereof of the present invention may comprise two LC CDRs selected from SEQ ID NO:3 (LC CDR1), SEQ ID NO:4 (LC CDR2), and SEQ ID NO:5 (LC CDR3). In some embodiments, a monoclonal antibody or the fragment thereof of the present invention may comprise three LC CDRs, wherein the three LC CDRs comprise SEQ ID NO:3 (LC CDR1), SEQ ID NO:4 (LC CDR2), and SEQ ID NO:5 (LC CDR3)).

```
LC CDR1
                                       SEQ ID NO: 3
KSSQSLLNSRTRKNYLA.

LC CDR2
                                       SEQ ID NO: 4
WASTRES.

LC CDR3
                                       SEQ ID NO: 5
KQSYNLRT.
```

In some embodiments, a monoclonal antibody or the fragment thereof of the present invention may further comprise a heavy chain (HC) complementarily determining region (HC CDR). In some embodiments, the HC CDR may comprise the amino acid sequence of SEQ ID NO:6 (HC CDR1), SEQ ID NO:7 (HC CDR2), or SEQ ID NO:8 (HC CDR3). In some embodiments, a monoclonal antibody or the fragment thereof of the present invention may further comprise two or more HC CDRs, e.g., two HC CDRs, three HC CDRs, or more. In some embodiments, a monoclonal antibody or the fragment thereof of the present invention may comprise two HC CDRs selected from SEQ ID NO:6 (HC CDR1), SEQ ID NO:7 (HC CDR2), or SEQ ID NO:8 (HC CDR3)). In some embodiments, a monoclonal antibody or the fragment thereof of the present invention may comprise three HC CDRs, wherein the three HC CDRs comprise SEQ ID NO:6 (HC CDR1), SEQ ID NO:7 (HC CDR2), and SEQ ID NO:8 (HC CDR3)).

```
HC CDR1
                                       SEQ ID NO: 6
SDFAWN.

HC CDR2
                                       SEQ ID NO: 7
YISYSGNTYYNPSLKS.

HC CDR3
                                       SEQ ID NO: 8
GSYYFDY.
```

In some embodiments, the monoclonal antibody or the fragment thereof of the present invention may bind to the C-terminus of human angiotensin-(1-12).

In some embodiments, the C-terminus of human angiotensin-(1-12) may comprise the amino acid sequence of SEQ ID NO:9.

```
Ang (1-12) C terminus
                            SEQ ID NO: 9
DRVYIHPFHLVI.
```

In some embodiments, the monoclonal antibody or the fragment thereof of the present invention may bind to an epitope within SEQ ID NO:9. In some embodiments, the monoclonal antibody or the fragment thereof of the present invention may bind an epitope that comprises at least five or more contiguous amino acids of the amino acid sequence of SEQ ID NO:9. In some embodiments, may bind to an epitope within SEQ ID NO:9 and comprises at least five or more contiguous amino acids of the amino acid sequence of SEQ ID NO:9. In some embodiments, the monoclonal antibody or the fragment thereof may bind to an epitope within and/or comprising the amino acid sequence of SEQ ID NO:9 or to an epitope having at least about 70% (e.g., about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%) sequence identity to SEQ ID NO:9 and/or wherein the monoclonal antibody or the fragment thereof does not effectively bind (e.g., has no or minimal binding) to an epitope within and/or comprising the amino acid sequence of one or more of SEQ ID NOs:20-22.

```
Angiotensin I
                            SEQ ID NO: 20
DRVYIHPFHL.

Angiotensin II
                            SEQ ID NO: 21
DRVYIHPF.

Angiotensin-(1-7)
                            SEQ ID NO: 22
DRVYIHP.
```

In some embodiments, the monoclonal antibody or the fragment thereof of the present invention may comprise a heavy chain variable region comprising an amino acid sequence having at least about 70% (e.g., about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%) sequence identity to SEQ ID NO:10.

```
HC variable region
                            SEQ ID NO: 10
MRVLILLWLFTAFPGILSDVQLQESGPGLVKPSQSLSLTCTVNGYSITSD

FAWNWIRQFPGNKLEWMGYISYSGNTYYNPSLKSRISITRDTSKNQFFLQ

LNSVTTEDTATYYCARGSYYFDYWGQGTTLTVSS.
```

In some embodiments, the monoclonal antibody or the fragment thereof of the present invention may comprise a light chain variable region comprising an amino acid sequence having at least about 70% (e.g., about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%) sequence identity to SEQ ID NO:11.

```
LC variable region.
                            SEQ ID NO: 11
MDSQAQVLILLLLWVSGTCGDIVMSQSPSSLAVSAGEKVTMSCKSSQSLL

NSRTRKNYLAWYQQKPGQSPKLLIYWASTRESGVPDRFTGSGSGTDFTLT

ISSVQAEDLAVYYCKQSYNLRTFGGGTKLEIK.
```

In some embodiments, the monoclonal antibody or the fragment thereof of the present invention may be configured for intracellular delivery. Configuration for intracellular delivery may be according to any conformation and/or formulation which allows for effective intracellular delivery. In some embodiments, configuring for intracellular delivery may comprise formulating the monoclonal antibody or the fragment thereof for intracellular delivery, e.g., a liposomal formulation, e.g., a lipid liposome and the like. The lipid layer employed can be of any conventional composition and can either contain cholesterol or can be cholesterol-free. The liposomes that are produced can be reduced in size, for example, through the use of standard sonication and homogenization techniques. The liposomal formulations can be lyophilized to produce a lyophilizate which can be reconstituted with a pharmaceutically acceptable carrier, such as water, to regenerate a liposomal suspension. In some embodiments, the monoclonal antibody or fragment thereof of the present invention may be configured as a chimeric antibody or fragment thereof, a CDR-grafted antibody or fragment thereof, a humanized antibody or fragment thereof, an Fc, a Fab, a Fab', a F(ab')2, a Fv, a disulfide linked Fv, a single chain antibody (scFv), a single domain antibody (dAb), a diabody, a multispecific antibody (e.g., a bispecific antibody) or fragment thereof, an anti-idiotypic antibody or fragment thereof, a bifunctional hybrid antibody or fragment thereof, a functionally active epitope-binding antibody fragment, an affibody, a nanobody, and any combination thereof. In some embodiments, the monoclonal antibody or the fragment thereof of the present invention may be a single-domain antibody (e.g., a nanobody).

In some embodiments, the monoclonal antibody or the fragment thereof of the present invention (e.g., as a single-domain antibody) may have a molecular weight of about 10,000 or 12,000 kiloDaltons to about 15,000 or 20,000 kiloDaltons, e.g., about 10K, 10.5K, 11K, 11.5K, 12K, 12.5K, 13K, 13.5K, 14K, 14.5K, 15K, 15.5K, 16K, 16.5K, 17K, 17.5K, 18K, 18.5K, 19K, 19.5K, or 20K kiloDaltons or any value or range therein. For example, in some embodiments, the monoclonal antibody or the fragment thereof of the present invention (e.g., as a single-domain antibody) may have a molecular weight of about 10K kiloDaltons to about 20K kiloDaltons, about 12K kiloDaltons to about 15K kiloDaltons, about 10.5K kiloDaltons to about 12K kiloDaltons, about 15K kiloDaltons to about 20K kiloDaltons, about 11K kiloDaltons to about 17K kiloDaltons, or about 10K, about 12K, about 15K, about 17K, or about 20K kiloDaltons.

A single-domain antibody of the present invention may be prepared via any standard method known in the field, as would be apparent to the skilled artisan upon review of the disclosures herein. For example, in some embodiments, a single-domain antibody of the present invention may be prepared using a VHH plasmid DNA construct.

In some embodiments, the monoclonal antibody or the fragment thereof of the present invention may reduce, inhibit, and/or block one or more angiotensin II pathological mechanisms and/or actions. Pathological mechanisms and/or actions of angiotensin II include any inherent mechanism and/or action known or later discovered. For example, in some embodiments, the monoclonal antibody or the fragment thereof reduces or inhibits pressor activity (e.g., vasopressor activity) of angiotensin-(1-12). In some embodiments, the monoclonal antibody or the fragment thereof reduces or inhibitors pressor activity (e.g., vasopressor activity) of endogenous human angiotensin-(1-12), such as but not limited to Ang-(1-12) that is in the circulation. In some embodiments, the monoclonal antibody or the fragment thereof reduces or inhibits an Ang-(1-12) constrictor response. In some embodiments, In some embodiments, the monoclonal antibody or the fragment thereof reduces or inhibitors pressor activity of human angiotensin-(1-12) and reduces or inhibits an Ang-(1-12) constrictor response. In some embodiments, the monoclonal antibody or the fragment thereof reduces or prevents angiotensin II production (e.g., angiotensin II intracellular production). In some embodiments, the monoclonal antibody or the fragment thereof is immunoneutralizing to angiotensin-(1-12). In some embodiments the monoclonal antibody or the fragment thereof fully neutralizes angiotensin-(1-12).

In some embodiments, the monoclonal antibody or the fragment thereof of the present invention may be a chimeric antibody or a fragment thereof.

In some embodiments, the monoclonal antibody or the fragment thereof of the present invention may be a humanized antibody or a fragment thereof.

Also provided herein is a pharmaceutical composition comprising the monoclonal antibody or the fragment thereof of the present invention, and a pharmaceutically acceptable carrier.

In the manufacture of a pharmaceutical composition according to embodiments of the present invention, the composition of this invention is typically admixed with, inter alia, a pharmaceutically acceptable carrier. By "pharmaceutically acceptable carrier" is meant a carrier that is compatible with other ingredients in the pharmaceutical composition and that is not harmful or deleterious to the subject. A "pharmaceutically acceptable" component such as a salt, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components include, without limitation, any of the standard pharmaceutical carriers such as phosphate buffered saline solutions, water, emulsions such as oil/water emulsion, microemulsions and various types of wetting agents. A pharmaceutically acceptable carrier can comprise, consist essentially of or consist of one or more synthetic components (e.g., components that do not naturally occur in nature), as are known in the art.

The carrier may be a solid or a liquid, or both, and is preferably formulated with the composition of this invention as a unit-dose formulation. The pharmaceutical compositions are prepared by any of the well-known techniques of pharmacy including, but not limited to, admixing the components, optionally including one or more accessory ingredients. Exemplary pharmaceutically acceptable carriers include, but are not limited to, sterile pyrogen-free water and sterile pyrogen-free physiological saline solution. Such carriers can further include protein (e.g., serum albumin) and sugar (sucrose, sorbitol, glucose, etc.). Also provided herein is an isolated nucleic acid molecule encoding the monoclonal antibody or the fragment thereof of the present invention.

In some embodiments, the nucleic acid molecule encoding the monoclonal antibody or fragment thereof of the present invention may comprise a nucleotide sequence having at least about 70% (e.g., about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%) sequence identity to one or more of SEQ ID NOs:12-19.

```
                                              SEQ ID NO: 12
TGTGCAAGAGGATCCTACTACTTTGACTACTGG.

SEQ ID NO: 13
TGCAAGCAATCTTATAATCTTCGGACGTTC.

LC CDR1
                                              SEQ ID NO: 14
AAATCCAGTCAGAGTCTGCTCAACAGTAGAACCCGAAAGAACTACTTG

GCT.

LC CDR2
                                              SEQ ID NO: 15
TGGGCATCCACTAGGGAATCT.

LC CDR3
                                              SEQ ID NO: 16
AAGCAATCTTATAATCTTCGGACG.

HC CDR1
                                              SEQ ID NO: 17
AGTGATTTTGCCTGGAAC

HC CDR2
                                              SEQ ID NO: 18
TACATAAGCTACAGTGGTAACACTTACTACAACCCATCTCTCAAAAGT.

HC CDR3
                                              SEQ ID NO: 19
GGATCCTACTACTTTGACTAC.
```

Monoclonal antibodies of the present invention may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) *Nature* 256:495-497; Kozbor, D. et al. (1985) *J. Immunol. Methods* 81:31-42; Cote, R. J. et al. (1983) *Proc. Natl. Acad. Sci.* 80:2026-2030; Cole, S. P. et al. (1984) *Mol. Cell Biol.* 62:109-120). Briefly, the procedure is as follows: an animal is immunized with antigen or immunogenic fragments or conjugates thereof. For example, haptenic oligopeptides of antigen can be conjugated to a carrier protein to be used as an immunogen. Lymphoid cells (e.g. splenic lymphocytes) are then obtained from the immunized animal and fused with immortalizing cells (e.g. myeloma or heteromyeloma) to produce hybrid cells. The hybrid cells are screened to identify those which produce the desired antibody.

Human hybridomas which secrete human antibody can be produced by the Kohler and Milstein technique. Although human antibodies are especially preferred for treatment of humans, in general, the generation of stable human-human hybridomas for long-term production of human monoclonal antibody can be difficult. Hybridoma production in rodents, especially mouse, is a very well established procedure and thus, stable murine hybridomas provide an unlimited source of antibody of select characteristics. As an alternative to human antibodies, the mouse antibodies can be converted to chimeric murine/human antibodies by genetic engineering techniques. See V. T. Oi et al., *Bio Techniques* 4(4):214-221 (1986); L. K. Sun et al., *Hybridoma* 5 (1986).

In addition, techniques developed for the production of "chimeric antibodies", the splicing of mouse antibody genes to human antibody genes to obtain a molecule with appropriate antigen specificity and biological activity can be used (S. L. Morrison, et al. *Proc. Natl. Acad. Sci.* 81, 6851-6855 (1984); M. S. Neuberger et al., *Nature* 312:604-608 (1984);

S. Takeda, S. et al., *Nature* 314:452-454 (1985)). Alternatively, techniques described for the production of single chain antibodies may be adapted, using methods known in the art, to produce epitope/antigen-specific single chain antibodies. Antibodies with related specificity, but of distinct idiotypic composition, may be generated by chain shuffling from random combinatorial immunoglobin libraries (D. R. Burton, *Proc. Natl. Acad. Sci.* 88, 11120-3 (1991)).

Antibodies may also be produced by inducing in vivo production in the lymphocyte population or by screening immunoglobulin libraries or panels of highly specific binding reagents as disclosed in the literature (R. Orlandi et al., *Proc. Natl. Acad. Sci.* 86, 3833-3837 (1989)); G. Winter et al., *Nature* 349, 293-299 (1991)).

Polyclonal antibodies used to carry out the present invention may be produced by immunizing a suitable animal (e.g., rabbit, goat, etc.) with the antigen to which monoclonal antibody binds, collecting immune serum from the animal, and separating the polyclonal antibodies from the immune serum, in accordance with known procedures. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

Antibodies that bind to the same epitope (i.e., the specific binding site) that is bound by the antibody of interest (e.g., antibody to Ang (1-12)) can be identified in accordance with known techniques, such as their ability to compete with labeled antibody to in binding to the epitope/antigen (e.g., Ang (1-12)) in a competitive binding assay.

Monoclonal antibodies specific for an epitope/antigen (e.g., Ang (1-12)) can be used to produce anti-idiotypic (paratope-specific) antibodies. See e.g., McNamara et al., *Science* 220, 1325-26 (1984), R. C. Kennedy, et al., *Science* 232,220 (1986). These antibodies resemble the epitope and thus can be used as an antigen to stimulate an immune response against the epitope, or to screen other antibodies for the ability to specifically bind to the same epitope bound by monoclonal antibody.

The epitope/antigen or fragment thereof (e.g., Ang (1-12)) can also be bound to a column (such as Protein A/G) and used to obtain purified antigen from a variety of sources, including human tissues/tumors and cancer cell lines that produce the antigen. Such purified antigen can then be used to produce additional antibodies (monoclonal and/or polyclonal) by methods described above. Some of these antibodies may react with the epitope while others can recognize different epitopes on the antigen (e.g., Ang (1-12)).

Accordingly, also provided herein is a hybridoma cell comprising the monoclonal antibody or the fragment thereof of the present invention and/or the isolated nucleic acid molecule of the present invention.

Also provided herein is a kit comprising the monoclonal antibody or the fragment thereof of, pharmaceutical composition, isolated nucleic acid molecule and/or hybridoma cell of the present invention, and information (e.g., instructions for use of the kit).

The information may be provided on a readable medium. The readable medium may comprise a label. The information may be directed towards a physician, pharmacist or patient. The information may comprise instructions for use of the components of the kit, such as in a manners described herein. These instructions may be provided in a variety of ways. For example, the information may include a table including a variety of weights or weight ranges appropriate dosages for each weight and/or weight range.

The information can be associated with the container, for example, by being written on a label (e.g., the prescription label or a separate label) adhesively affixed to a container, included inside a container as a written package insert, applied directly to the container such as being printed on the wall of a box or blister pack, or attached as by being tied or taped, for example as an instructional card affixed to the neck of a bottle via a string, cord or other line, lanyard or tether type device.

The kit may further comprise a container and/or a package suitable for commercial sale. The container can be in any conventional shape or form as known in the art which is made of a pharmaceutically acceptable material, such as a paper or cardboard box, a glass or plastic bottle or jar, a re-sealable bag, or a blister pack with individual dosages for pressing out of the pack according to a therapeutic schedule. More than one container can be used together in a single package. For example, tablets may be contained in a blister pack which is in turn contained within a box.

Methods

The antibodies, fragments thereof, nucleic acid molecules and/or compositions of this invention are intended for use as therapeutic agents. The compositions described herein can be formulated for use as reagents and/or for administration in a pharmaceutical carrier in accordance with known techniques. See, e.g., Remington, The Science and Practice of Pharmacy (Latest Edition).

One aspect of the present invention provides a method of reducing, inhibiting, and/or blocking one or more angiotensin II pathological mechanisms and/or actions, the method comprising contacting angiotensin-(1-12) and the monoclonal antibody or the fragment thereof of the present invention, thereby reducing, inhibiting, and/or blocking one or more Ang II pathological mechanisms and/or actions In some embodiments, contacting angiotensin-(1-12) and the monoclonal antibody or the fragment thereof of the present invention comprises administering the monoclonal antibody or the fragment thereof to a subject, optionally in an effective amount.

Another aspect of the present invention provides a method of treating and/or preventing a disorder in a subject, the method comprising administering to the subject a therapeutically effective amount of the monoclonal antibody or the fragment thereof of the present invention, thereby treating and/or preventing the disorder in the subject.

In some embodiments of the methods disclosed herein, the monoclonal antibody or the fragment thereof of the present invention may reduce or inhibit enzymatic cleavage of angiotensin-(1-12) to form angiotensin II, e.g., may reduce or inhibit enzymatic cleavage by about 5, 10, 15, 20, 25, 30, 35, 40, 45, 50, 55, 60, 65, 70, 75, 80, 85, 90, 95, 96, 97, 98, 99, or 100% or more, or any value or range therein.

In some embodiments, the monoclonal antibody or the fragment thereof of the present invention may reduce, inhibit, or block one or more angiotensin II pathological mechanisms and/or actions.

For example, in some embodiments, the monoclonal antibody or the fragment thereof may reduce or inhibit pressor activity (e.g., vasopressor activity) of angiotensin-(1-12) (e.g., endogenous angiotensin-(1-12) that is optionally in circulation in the subject) and/or may reduce or inhibit an angiotensin-(1-12) constrictor response. In some embodiments, the monoclonal antibody or the fragment thereof may reduce or inhibit pressor activity (e.g., vasopressor activity) of angiotensin-(1-12) (e.g., endogenous angiotensin-(1-12) that is optionally in circulation in the subject) and/or may reduce or inhibit an angiotensin-(1-12) constrictor response in the subject.

In some embodiments, the monoclonal antibody or the fragment thereof may reduce or prevent angiotensin II production, including but not limited to, angiotensin II intracellular production.

In some embodiments, the monoclonal antibody or the fragment thereof may be immunoneutralizing to angiotensin-(1-12) and/or may fully neutralize angiotensin-(1-12).

In some embodiments, the monoclonal antibody or the fragment thereof may reduce arterial pressure (e.g., baseline arterial pressure) in the subject.

In some embodiments, the monoclonal antibody or the fragment thereof may not modify the heart rate of the subject. In some embodiments, the monoclonal antibody or fragment thereof may modify the heart rate of the subject by about ±10% or less (e.g., increase the heart rate by about 1, 2, 3, 4, 5, 6, 7, 8, 9, or 10% or less, or any value or range therein; e.g., decrease the heart rate by about 1, 2, 3, 4, 5, 6, 7, 8, 9, or 10% or less, or any value or range therein).

Disorders for treatment by the methods and compositions of the present application include any disorders associated with aberrant expression and/or activity of angiotensin-II. For example, in some embodiments, the disorder may be associated with elevated angiotensin-II and/or the subject may have an elevated level of angiotensin-II. Further non-limiting examples of disorders of the present invention include cardiovascular disorder (e.g., cardiovascular disease), cancer, diabetes mellitus, disease of the connective tissue, rheumatic disease, chronic renal failure, autoimmune disorder, hematopoietic disorder, acute respiratory distress syndrome (ARDS), viral infection, or any combination thereof. In some embodiments, the disorder is cardiovascular disease. In some embodiments, the disorder is a coronavirus disease (e.g., coronavirus infection and/or related sequelae, e.g., COVID-19).

In some embodiments of the methods disclosed herein, the monoclonal antibody or the fragment thereof binds to angiotensin-(1-12) at a half maximal effective concentration ($EC_{50}$) of about 150 fmol or less, e.g., about 150, 140, 130, 120, 110, 110, 90, 80, 70 or 60 fmol or any value or range therein. For example, in some embodiments, the monoclonal antibody or the fragment thereof binds to angiotensin-(1-12) at an $EC_{50}$ of about 60 fmol to about 150 fmol, about 60 fmol to about 100 fmol, about 100 fmol to about 150 fmol, about 60 fmol, about 70 fmol, about 85 fmol, about 100 fmol, about 125 fmol, or about 150 fmol. In some embodiments, the monoclonal antibody or the fragment thereof binding to angiotensin-1(1-12) comprises binding to an epitope within SEQ ID NO:9.

In some embodiments, the monoclonal antibody or the fragment thereof has cross-reactivity with angiotensinogen (AGT) protein or AGT-derived angiotensin peptides (e.g., angiotensin peptides including, but not limited to, angiotensin I, angiotensin II, angiotensin-(1-7)) in an amount of about 0.005% or less, e.g., about 0.005, 0.004, 0.003, 0.002, 0.001% or any value or range therein. For example, in some embodiments, the monoclonal antibody or the fragment thereof has cross-reactivity with angiotensinogen (AGT) protein or AGT-derived angiotensin peptides (e.g., angiotensin I, angiotensin II, and/or angiotensin-(1-7)) in an amount of about 0.005% to about 0.001%, about 0.0045% to about 0.01%, or about 0.005% to about 0.0005%. In some embodiments, the monoclonal antibody or the fragment thereof has cross-reactivity with angiotensinogen (AGT) protein or AGT-derived angiotensin peptides (e.g., angiotensin I, angiotensin II, and/or angiotensin-(1-7)) in an amount of about 0.005%, about 0.004%, about 0.003%, about 0.002%, about 0.001%, or about 0.0005%.

In some embodiments, the monoclonal antibody or the fragment thereof of the present invention may inhibit a pressor activity (e.g., activity of inducing vasoconstriction) of angiotensin-(1-12) and/or angiotensin II. For example, in some embodiments, the monoclonal antibody or the fragment thereof of the present invention may inhibit a pressor activity (e.g., activity of inducing vasoconstriction) of angiotensin-(1-12) and/or angiotensin II for about 10, 20, 30, 40, 50, 60, 70, 80, 90, 100 minutes (or any value or range therein) or more following contacting and/or administering of the monoclonal antibody or the fragment thereof.

In some embodiments of the methods disclosed herein, the monoclonal antibody or the fragment thereof may be encoded by an isolated nucleic acid molecule (e.g., an isolated nucleic acid molecule of the present invention as described herein).

Also provided herein is any antibody, composition, article, system, and/or method as described and/or shown herein.

The present invention may be as defined in any one of the following numbered paragraphs.

1. A monoclonal antibody or a fragment thereof, wherein the monoclonal antibody or the fragment thereof binds to human angiotensin-(1-12).
2. The monoclonal antibody or the fragment thereof of paragraph 1, wherein the monoclonal antibody or the fragment thereof comprises a heavy chain variable region comprising a VDJ junction region comprising an amino acid sequence having at least about 70%, 75%, 80%, 85%, 90%, 95%, or 100% sequence identity to SEQ ID NO:1.
3. The monoclonal antibody or the fragment thereof of paragraph 1 or 2, wherein the monoclonal antibody or the fragment thereof comprises a light chain variable region comprising a VDJ junction region comprising an amino acid sequence having at least about 70%, 75%, 80%, 85%, 90%, 95%, or 100% sequence identity to SEQ ID NO:2.
4. A monoclonal antibody or a fragment thereof, wherein the monoclonal antibody or the fragment thereof comprises a heavy chain variable region comprising a VDJ junction region comprising an amino acid sequence having at least about 70%, 75%, 80%, 85%, 90%, 95%, or 100% sequence identity to SEQ ID NO:1.
5. The monoclonal antibody or the fragment thereof of paragraph 4, wherein the monoclonal antibody or the fragment thereof binds to human angiotensin-(1-12).
6. The monoclonal antibody or the fragment thereof of paragraph 4 or 5, wherein the monoclonal antibody or the fragment thereof comprises a light chain variable region comprising a VDJ junction region comprising an amino acid sequence having at least about 70%, 75%, 80%, 85%, 90%, 95%, or 100% sequence identity to SEQ ID NO:2.
7. A monoclonal antibody or a fragment thereof, wherein the monoclonal antibody or the fragment thereof comprises a light chain variable region comprising a VDJ junction region comprising an amino acid sequence having at least about 70%, 75%, 80%, 85%, 90%, 95%, or 100% sequence identity to SEQ ID NO:2.

8. The monoclonal antibody or the fragment thereof of paragraph 7, wherein the monoclonal antibody or the fragment thereof binds to human angiotensin-(1-12).
9. The monoclonal antibody or the fragment thereof of paragraph 7 or 8, wherein the monoclonal antibody or the fragment thereof comprises a heavy chain variable region comprising a VDJ junction region comprising an amino acid sequence having at least about 70%, 75%, 80%, 85%, 90%, 95%, or 100% sequence identity to SEQ ID NO:1.
10. The monoclonal antibody or the fragment thereof of any one of paragraphs 1-9, further comprising a light chain (LC) complementarity determining region (LC CDR) having a sequence of SEQ ID NO:3 (LC CDR1), SEQ ID NO:4 (LC CDR2), or SEQ ID NO:5 (LC CDR3), optionally wherein the monoclonal antibody or the fragment thereof comprises two LC CDRs (e.g., two LC CDRs selected from SEQ ID NO:3 (LC CDR1), SEQ ID NO:4 (LC CDR2), and SEQ ID NO:5 (LC CDR3)) or three LC CDRs (i.e., comprises SEQ ID NO:3 (LC CDR1), SEQ ID NO:4 (LC CDR2), and SEQ ID NO:5 (LC CDR3)).
11. The monoclonal antibody or the fragment thereof of any one of paragraphs 1-10, further comprising a heavy chain (HC) complementarity determining region (HC CDR) having a sequence of SEQ ID NO:6 (HC CDR1), SEQ ID NO:7 (HC CDR2), or SEQ ID NO:8 (HC CDR3), optionally wherein the monoclonal antibody or the fragment thereof comprises two HC CDRs (e.g., two HC CDRs selected from SEQ ID NO:6 (HC CDR1), SEQ ID NO:7 (HC CDR2), or SEQ ID NO:8 (HC CDR3)) or three HC CDRs (i.e., comprises SEQ ID NO:6 (HC CDR1), SEQ ID NO:7 (HC CDR2), and SEQ ID NO:8 (HC CDR3)).
12. The monoclonal antibody or the fragment thereof of any one of paragraphs 1-11, wherein the monoclonal antibody or the fragment thereof binds to the C-terminus of human angiotensin-(1-12), optionally wherein the C-terminus of human angiotensin-(1-12) comprises an amino acid sequence of SEQ ID NO:9.
13. The monoclonal antibody or the fragment thereof of any one of paragraphs 1-12, wherein the monoclonal antibody or the fragment thereof binds to an epitope within and/or that comprises at least five or more contiguous amino acids of the amino acid sequence of SEQ ID NO:9, optionally wherein the monoclonal antibody or the fragment thereof binds to an epitope within and/or comprising the amino acid sequence of SEQ ID NO:9 or to an epitope having at least about 70%, 75%, 80%, 85%, 90%, 95%, or 100% sequence identity to SEQ ID NO:9 and/or wherein the monoclonal antibody or the fragment thereof does not effectively bind (e.g., has no or minimal binding) to an epitope within and/or comprising the amino acid sequence of one or more of SEQ ID NOs:20-22.
14. The monoclonal antibody or the fragment thereof of any one of paragraphs 1-13, wherein the monoclonal antibody or the fragment thereof comprises a heavy chain variable region comprising an amino acid sequence having at least about 70%, 75%, 80%, 85%, 90%, 95%, or 100% sequence identity to SEQ ID NO:10.
15. The monoclonal antibody or the fragment thereof of any one of paragraphs 1-14, wherein the monoclonal antibody or the fragment thereof comprises a light chain variable region comprising an amino acid sequence having at least about 70%, 75%, 80%, 85%, 90%, 95%, or 100% sequence identity to SEQ ID NO:11.
16. The monoclonal antibody or the fragment thereof of any one of paragraphs 1-15, wherein the monoclonal antibody or the fragment thereof is configured for intracellular delivery, optionally wherein the monoclonal antibody or the fragment thereof is a single-domain antibody (e.g., a nanobody) and/or has a molecular weight of about 10,000 or 12,000 kiloDaltons to about 15,000 or 20,000 kiloDaltons, further optionally wherein the single-domain antibody is prepared using a VHH plasmid DNA construct.
17. The monoclonal antibody or the fragment thereof of any one of paragraphs 1-16, wherein the monoclonal antibody or the fragment thereof reduces, inhibits, or blocks one or more angiotensin II pathological mechanisms and/or actions.
18. The monoclonal antibody or the fragment thereof of any one of paragraphs 1-17, wherein the monoclonal antibody or the fragment thereof reduces or inhibits pressor activity (e.g., vasopressor activity) of angiotensin-(1-12) (e.g., endogenous human angiotensin-(1-12) (Ang-(1-12) that is optionally in circulation) and/or reduces or inhibits an Ang-(1-12) constrictor response.
19. The monoclonal antibody or the fragment thereof of any one of paragraphs 1-18, wherein the monoclonal antibody or the fragment thereof reduces or prevents angiotensin II production (e.g., angiotensin II intracellular production).
20. The monoclonal antibody or the fragment thereof of any one of paragraphs 1-19, wherein the monoclonal antibody or the fragment thereof is immunoneutralizing to angiotensin-(1-12) and/or wherein the monoclonal antibody or the fragment thereof fully neutralizes angiotensin-(1-12).
21. The monoclonal antibody or the fragment thereof of any one of paragraphs 1-20, which is a chimeric antibody or a fragment thereof.
22. The monoclonal antibody or the fragment thereof of any one of paragraphs 1-21, which is a humanized antibody or a fragment thereof.
23. A pharmaceutical composition comprising the monoclonal antibody or the fragment thereof of any one of paragraphs 1-22 and a pharmaceutically acceptable carrier.
24. An isolated nucleic acid molecule encoding the monoclonal antibody or the fragment thereof of any one of paragraphs 1-22.
25. The isolated nucleic acid molecule of paragraph 24, wherein the nucleic acid molecule comprises a sequence having at least about 70%, 75%, 80%, 85%, 90%, 95%, or 100% sequence identity to one or more of SEQ ID NOs:12-19.
26. A hybridoma cell comprising the monoclonal antibody or the fragment thereof of any one of paragraphs 1-22 and/or the isolated nucleic acid molecule of any one of paragraphs 24-25.
27. A kit comprising the monoclonal antibody or the fragment thereof of any one of paragraphs 1-22, the pharmaceutical composition of paragraph 23, the isolated nucleic acid molecule of any one of paragraphs 24-25 and/or the hybridoma cell of paragraph 26 and instructions for use of the kit.
28. A method of reducing, inhibiting, and/or blocking one or more angiotensin II pathological mechanisms and/or actions, the method comprising contacting angiotensin- (1-12) and the monoclonal antibody or the fragment thereof of any one of paragraphs 1-22, thereby reducing, inhibiting, and/or blocking one or more Ang II pathological mechanisms and/or actions.

29. The method of paragraph 28, wherein contacting angiotensin-(1-12) and the monoclonal antibody or the fragment thereof comprises administering the monoclonal antibody or the fragment thereof to a subject, optionally in an effective amount.

30. A method of treating and/or preventing a disorder in a subject, the method comprising administering to the subject a therapeutically effective amount of the monoclonal antibody or the fragment thereof of any one of paragraphs 1-22, thereby treating and/or preventing the disorder in the subject 31. The method of any one of paragraphs 28-30, wherein the monoclonal antibody or the fragment thereof reduces or inhibits enzymatic cleavage of angiotensin-(1-12) to form angiotensin II.

32. The method of any one of paragraphs 28-31, wherein the monoclonal antibody or the fragment thereof reduces, inhibits, or blocks one or more angiotensin II pathological mechanisms and/or actions.

33. The method of any one of paragraphs 28-32, wherein the monoclonal antibody or the fragment thereof reduces or inhibits pressor activity (e.g., vasopressor activity) of angiotensin-(1-12) (e.g., endogenous angiotensin-(1-12) that is optionally in circulation in the subject) and/or reduces or inhibits an angiotensin-(1-12) constrictor response optionally in the subject.

34. The method of any one of paragraphs 28-33, wherein the monoclonal antibody or the fragment thereof reduces or prevents angiotensin II production (e.g., angiotensin II intracellular production).

35. The method of any one of paragraphs 28-34, wherein the monoclonal antibody or the fragment thereof is immunoneutralizing to angiotensin-(1-12) and/or wherein the monoclonal antibody or the fragment thereof fully neutralizes angiotensin-(1-12).

36. The method of any one of paragraphs 30-35, wherein the monoclonal antibody or the fragment thereof reduces arterial pressure (e.g., baseline arterial pressure) in the subject.

37. The method of any one of paragraphs 30-36, wherein the monoclonal antibody or the fragment thereof does not modify or modifies by about ±10% or less heart rate of the subject.

38. The method of any one of paragraphs 30-37, wherein the disorder is associated with elevated angiotensin-II and/or the subject has an elevated level of angiotensin-II.

39. The method of any one of paragraphs 30-8, wherein the disorder is a cardiovascular disorder (e.g., cardiovascular disease), cancer, diabetes mellitus, disease of the connective tissue, rheumatic disease, chronic renal failure, autoimmune disorder, hematopoietic disorder, acute respiratory distress syndrome (ARDS), viral infection, or any combination thereof.

40. The method of paragraph 39, wherein the disorder is cardiovascular disease.

41. The method of paragraph 39, wherein the disorder is a coronavirus disease (e.g., COVID-19).

42. The method of any one of paragraphs 28-41, wherein the monoclonal antibody or the fragment thereof binds to angiotensin-(1-12) (e.g., to an epitope within SEQ ID NO:9) at a half maximal effective concentration ($EC_{50}$) of about 150 fmol or less (e.g., about 150, 140, 130, 120, 110, 110, 90, 80, 70 or 60 fmol or any value or range therein, e.g., about 60 fmol to about 150 fmol).

43. The method of any one of paragraphs 28-42, wherein the monoclonal antibody or the fragment thereof has cross-reactivity with angiotensinogen (AGT) protein or AGT-derived angiotensin peptides (e.g., angiotensin I, angiotensin II, angiotensin-(1-7)) in an amount of about 0.005% or less (e.g., about 0.005, 0.004, 0.003, 0.002, 0.001% or any value or range therein).

44. The method of any one of paragraphs 28-43, wherein the monoclonal antibody or the fragment thereof inhibits a pressor activity (e.g., activity of inducing vasoconstriction) of angiotensin-(1-12) and/or angiotensin II optionally for about 10, 20, 30, 40, 50, 60, 70, 80, 90, 100 minutes or more following contacting and/or administering of the monoclonal antibody or the fragment thereof.

45. The method of any one of paragraphs 28-44, wherein the monoclonal antibody or the fragment thereof is encoded by the isolated nucleic acid molecule of any one of paragraphs 24-25.

46. An antibody, composition, article, system, and/or method as described and/or shown herein.

The present invention is explained in greater detail in the following non-limiting examples.

EXAMPLES

Example 1

Total RNA was isolated from hybridoma cells following the technical manual of TRIzol® Reagent. Total RNA was then reverse-transcribed into cDNA using either isotype-specific anti-sense primers or universal primers following the technical manual of PrimeScript™ 1st Strand cDNA Synthesis Kit. Antibody fragments of heavy chain and light chain were amplified according to the standard operating procedure (SOP) of rapid amplification of cDNA ends (RACE) of GenScript. Amplified antibody fragments were cloned into a standard cloning vector separately. Colony PCR was performed to screen for clones with inserts of correct sizes. The consensus sequence was provided. Table 1 indicates resultant IMGT Analysis of V(D)J Junctions. Antibody sequences of Clone #-14B3 are provided below:

```
Heavy chain: DNA sequence (402 bp)
                                              SEQ ID NO: 25
Signal sequence-FR1-CDR1-FR2-CDR2-FR3-CDR3-FR4
ATGAGAGTGCTGATTCTTTTGTGGCTGTTCACAGCCTTTCCTGGTATCCTGTCTGA

TGTGCAGCTTCAGGAGTCGGGACCTGGCCTGGTGAAACCCTCTCAGTCTCTGTCCCTC

ACCTGCACTGTCAACGGCTACTCAATCACCAGTGATTTTGCCTGGAACTGGATCCGG

CAGTTTCCAGGAAACAAACTGGAGTGGATGGGCTACATAAGCTACAGTGGTAACAC
```

-continued

```
TTACTACAACCCATCTCTCAAAAGTCGAATCTCTATCACTCGAGACACATCCAAGAA

CCAGTTCTTCCTGCAGTTGAATTCTGTGACTACTGAGGACACAGCCACATATTACTGTG

CAAGAGGATCCTACTACTTTGACTACTGGGGCCAAGGCACCACTCTCACAGTCTCCT

CA.
```

Heavy chain: Amino acid sequence (134 aa)
SEQ ID NO: 26
Signal peptide-*FR1*-CDR1-*FR2*-CDR2-*FR3*-CDR3-*FR4*
MRVLILLWLFTAFPGILS*DVQLQESGPGLVKPSQSLSLTCTVNGYSIT*SDFAWN*WIRQFP*

*GNKLEWMGY*ISYSGNTYYNPSLKS*RISITRDTSKNQFFLQLNSVTTEDTATYYC*ARGSYY

FDY*WGQGTTLTVSS*.

Light chain: DNA sequence (396 bp)
SEQ ID NO: 27
Signal sequence-*FR1*-CDR1-*FR2*-CDR2-*FR3*-CDR3-*FR4*
```
ATGGATTCACAGGCCCAGGTTCTTATATTGCTGCTGCTATGGGTATCTGGTACCT

GTGGGGACATTGTGATGTCACAGTCTCCATCCTCCCTGGCTGTGTCAGCAGGAGAGAA

GGTCACTATGAGCTGCAAATCCAGTCAGAGTCTGCTCAACAGTAGAACCCGAAAG

AACTACTTGGCTTGGTACCAGCAGAAACCAGGGCAGTCTCCTAAACTGCTGATCTACT

GGGCATCCACTAGGGAATCTGGGGTCCCTGATCGCTTCACAGGCAGTGGATCTGGG

ACAGATTTCACTCTCACCATCAGCAGTGTGCAGGCTGAAGACCTGGCAGTTTATTACTG

CAAGCAATCTTATAATCTTCGGACGTTCGGTGGAGGCACCAAGTTGGAAATCAAA.
```

Light chain: Amino acid sequence (132 aa)
SEQ ID NO: 28
Signal peptide-*FR1*-CDR1-*FR2*-CDR2-*FR3*-CDR3-*FR4*
MDSQAQVLILLLLWVSGTCG*DIVMSQSPSSLAVSAGEKVTMSCKSSQSLLNSRTRKNY

LA*WYQQKPGQSPKLLIY*WASTRES*GVPDRFTGSGSGTDFTLTISSVQAEDLAVYYC*KQSY

NLRT*FGGGTKLEIK*.

Example 2

A molecular approach to treating hypertension may be achieved by neutralizing angiotensin-(1-12). Using a newly engineered monoclonal antibody (mAb) against the C-terminus of human angiotensin-(1-12), we performed a biochemical characterization in concert with direct in vivo and ex vivo (carotid artery strips) assessments of immunoneutralization of angiotensin-(1-12) vasoconstrictor activity in 12 (6 females) transgenic hypertensive rats expressing the human angiotensinogen gene and its Sprague Dawley controls [12 (6 females)].

Changes in arterial pressure and heart rate in anesthetized instrumented rats were measured before and following intravenous angiotensin-(1-12) [dose range: 75-300 pmol/kg] injections in the absence and presence of the mAb (30 mg/kg). Immunoneutralization of circulating Ang-(1-12) produced: a)—complete inhibition of the pressor action of intravenous angiotensin-(1-12); b)—prevented Ang-(1-12) constrictor responses in carotid artery rings; and c)—induced a sustained fall in baseline arterial pressure only in the transgenic rats for the entire duration of the experiments (>90 min). Supporting the mAb exclusiveness to human angiotensin-(1-12), the Ang-(1-12) mAb had no effect on comparable dose-related vasoconstrictor responses to Ang II, pre-immune IgG, or the rat sequence of the substrate.

We conclude that this highly specific angiotensin-(1-12) mAb can suppress the vasoconstrictor actions of the substrate administered in the systemic circulation or in the bath irrigating isolated carotid artery strips. The demonstration that this mAb by itself, induced a fall in arterial pressure in human angiotensinogen-dependent transgenic hypertensive rats reinforces the proof of concept necessary to explore its long-term antihypertensive actions in the progression of primary hypertension.

We report here the effects of acute immunoneutralization of Ang-(1-12) in the circulation of normal Sprague Dawley (SD) rats and transgenic hypertensive rats [TGR(hAGT) L1623] expressing the human sequence of the AGT gene[20-22] by means of a selective monoclonal antibody (mAb) engineered by us. This report is complemented by parallel assessment of the ability for h-Ang-(1-12) mAbs to block the contractile ability of the Ang II-generating substrate in isolated carotid artery rings from SD and TGR(hAGT) L1623 rats.

Prior to the experiments, 10-12 week-old rats, housed in a room maintained at 22° C. (12-hour light/dark cycle), were fed a chow diet containing a daily intake of 17 mmol of sodium and 28 mmol of potassium per 100 g of solid weight. Rats were randomly assigned to the experimental procedure based on sex, date of birth, and strain as recommended in the ARRIVE guidelines.[23] The studies were performed in 26 Sprague Dawley rats and 42 transgenic rats expressing the human AGT gene in their genome.

All data are shown as mean±SE. Statistical analysis was performed using Prism version 8.0 (GraphPad, LLC, San Diego, CA). Normal data distribution was evaluated using Kolmogorov-Smirnov goodness-of-fit tests. Student's t-test was used for between group comparisons while One- and Two-way analysis of variance addressed assessment of one or more independent variables. For the studies employing arterial strips, the average response of four segments per artery tested with each pharmacological agent was used in all cases. A 2-sided p<0.05 was considered statistically significant.

The custom-made and protein L purified mAb IgG is highly specific, recognizing only the C-terminus of the h-Ang-(1-12) sequence (FIG. 1). The mAb is highly specific to the carboxyl terminal (—COOH) of the h-Ang-(1-12) peptide because it does not recognize the C-terminal amide modified (—CONH2) hAng-(1-12) sequence (FIG. 1). Furthermore, the mAb does not cross react with purified AGT (human and rat) or AGT-derived angiotensin peptides.

Figure 2:
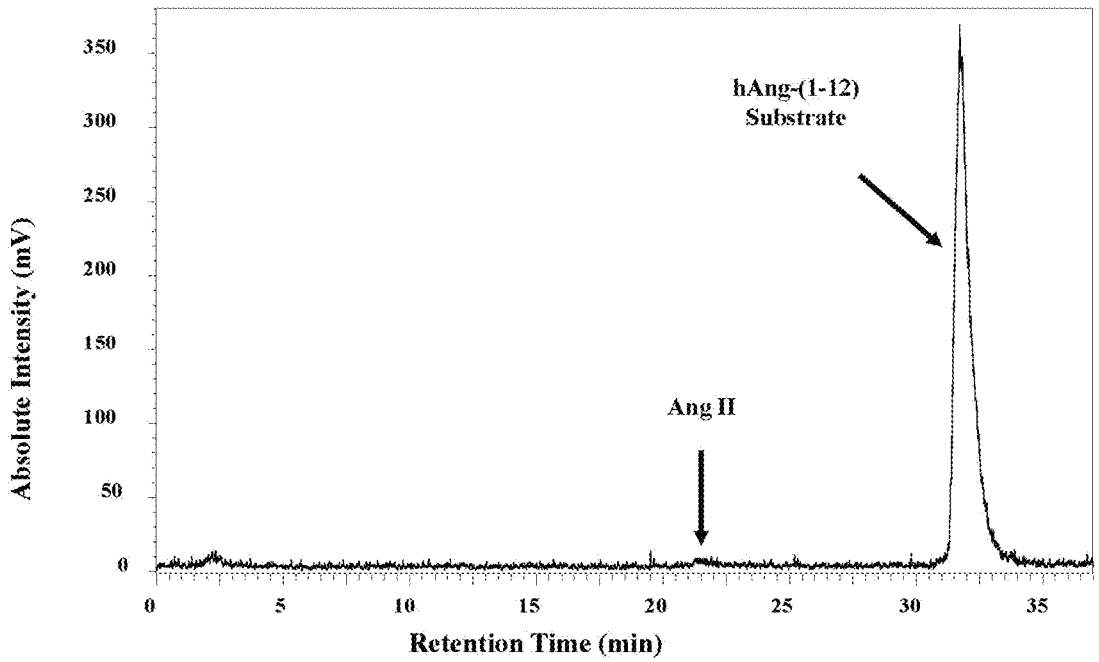
FIG. 2 shows a chromatogram indicating the stability of the h-Ang-(1-12)-mAb incubated for 7 days at 37° C. in rat serum. The mAb completely neutralizes the h-Ang-(1-12) substrate and prevents the Ang II product formation by recombinant human chymase.

As shown in FIG. 2, the h-Ang-(1-12) substrate was completely neutralized by the mAb pre-incubated for 7 day in rat serum. After analyzing the HPLC chromatogram, we found that 99% of the h-Ang-(1-12) substrate remained intact and only a trace amount (<1%) of the Ang II product formation were detected in the reaction mixture on the HPLC. These data demonstrate that the h-Ang-(1-12) mAb generated in our laboratory is highly specific for the human Ang-(1-12) amino acid sequence. The h-Ang-(1-12) mAb continues to exhibit a sustained immuno-neutralizing capacity even after being incubated at 37° C. with human plasma for as long as 7 days.

Figure 3:
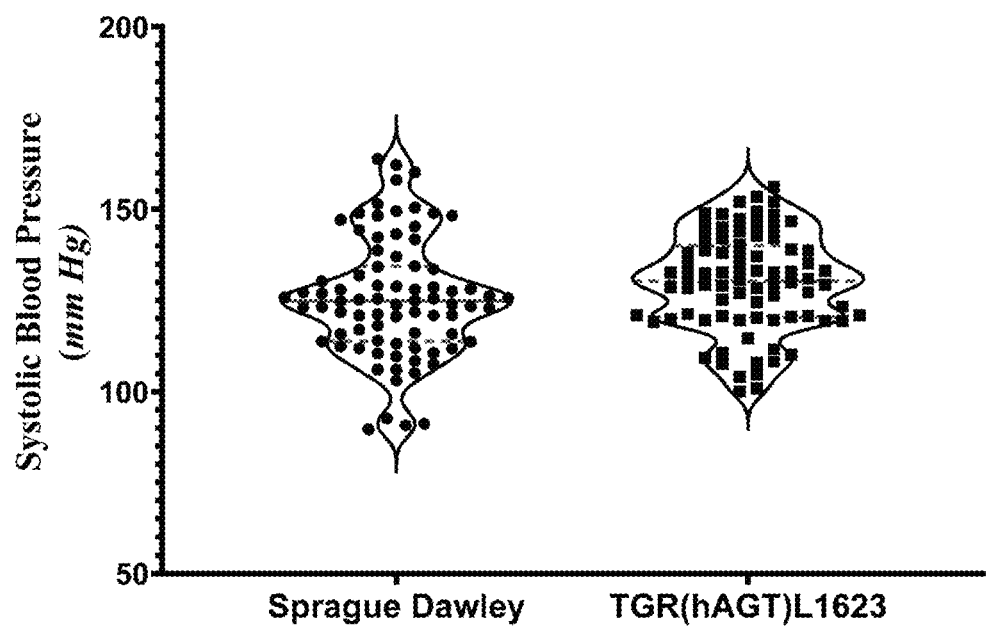
FIG. 3 shows Violin plots of the baseline systolic (top panel) and diastolic (bottom panel) blood pressures of 40 anesthetized Sprague Dawley (SD) rats and 40 transgenic rats expressing the human angiotensinogen gene [TGR (hAGT)L1623]. Horizontal lines shown in the plots are the median and upper and lower quartiles of the corresponding blood pressure values.
Figure 3:
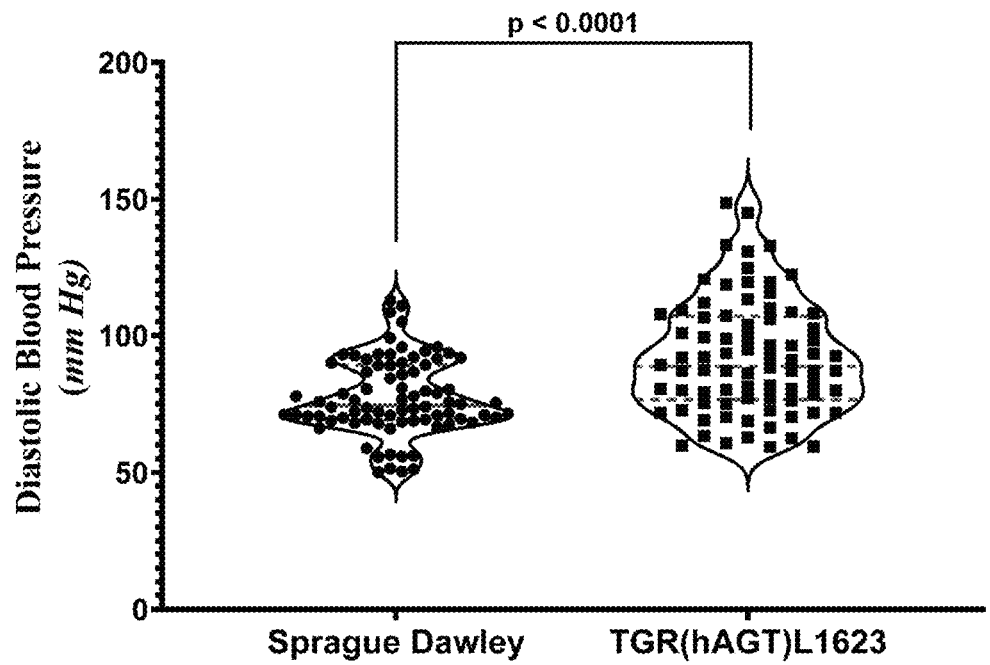

Blockade of Ang-(1-12) Systemic Pressor Effects in TGR (hAGT)L1623 and SD rats. Baseline systolic arterial pressure averaged 126±2 mm Hg (95% CI: 122-129 mm Hg) and 130±1 mm Hg (95% CI: 127-133 mm Hg) in 20 anesthetized SD and 20 TGR(hAGT)L1623 rats (p>0.05), respectively. Corresponding averages for diastolic arterial pressure are 77±2 mm Hg (95% CI: 74-87 mm Hg) in SD rats and 92±2 mm Hg (95% CI: 81-97 mm Hg) in TGR(hAGT)L1623 rats (p<0.0001). The distribution of the blood pressure data and probability density in the two groups are illustrated in FIG. 3. Baseline heart rate did not differ between anesthetized SD and TGR(hAGT)L1623 rats (SD: 318±3 beats/min versus 314±4 beats/min in TGR(hAGT)L1623; p>0.05). On the other hand, female SD rats at baseline had lower values of blood pressure and heart rate while in TGR(hAGT)L1623 rats sex differences at baseline showed statistical significance for systolic and mean arterial pressure (Table 2).

Figure 4:
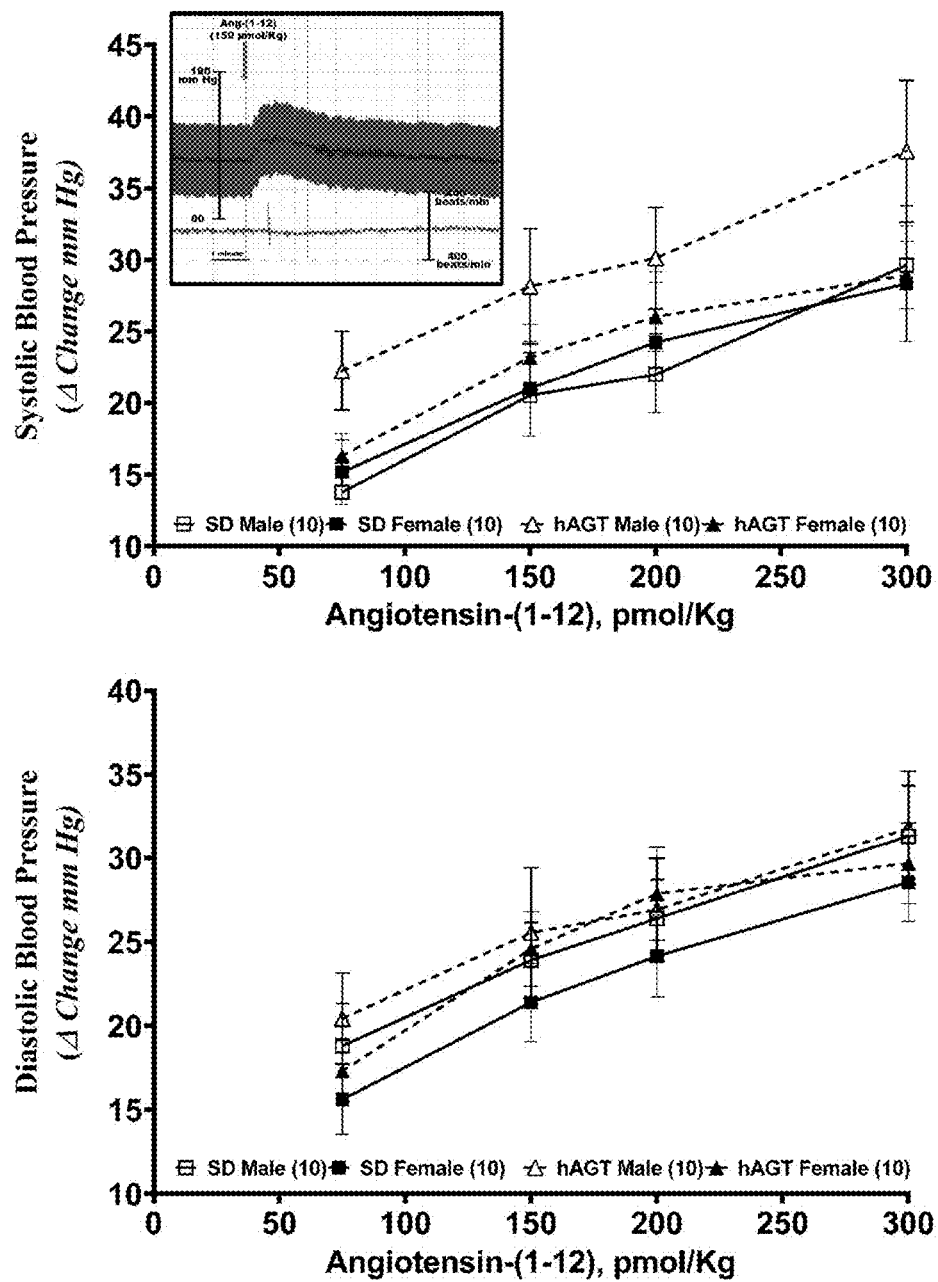
FIG. 4 shows data plots of mean change in peak systolic (top panel) and peak diastolic (bottom panel) arterial pressure produced by the administration of Ang-(1-12) (dose range: 75-300 pmol/kg) in male and female Sprague Dawley and TGR(hAGT)L1623 rats.

Intravenous delivery of h-Ang-(1-12), at doses between 75 pmol/kg and 300 pmol/kg, elicited rapid and dose-dependent increases in mean arterial pressure that peaked at +32.45±1.08 sec in SD rats and +36.20±1.52 sec in TGR (hAGT)L1623 rats (p<0.05). Differences between the two strains in the time to peak blood pressure response are due to the wider dispersion of values in the transgenic rats (SD 95% CI: 30.29-34.61 sec versus 33.17-39.23 sec in TGR (hAGT)L1623 rats). As illustrated in FIG. 4, the peak change in systolic blood pressure in male transgenic rats challenged with the h-Ang-(1-12) is greater than those recorded in the male SD controls (F=10.30, DFn=1, DFd=72, p<0.02). A similar effect of sex on the peak changes in diastolic blood pressure is not present in female TGR(hAGT)L1623 rats when compared with corresponding changes in diastolic blood pressure in female SD rats. Furthermore, sex does no influence the magnitude of the peak changes in systolic and diastolic blood pressure responses between male and female SD rats (FIG. 4).

Figure 5:
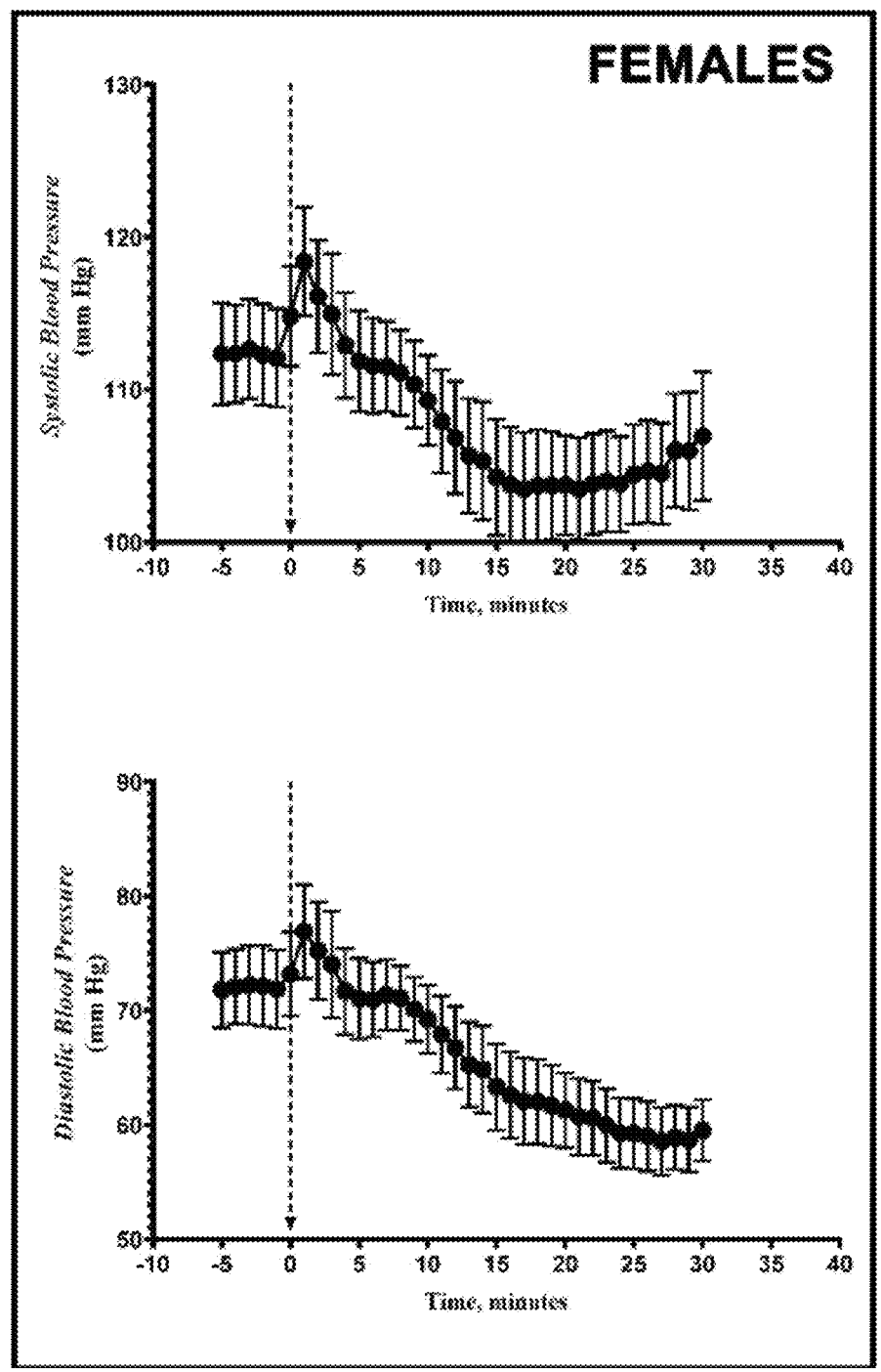
FIG. 5 shows data plots indicating the immunoneutralization of endogenous Ang-(1-12) in both female and male rats expressing the human angiotensinogen transgene [TGR (hAGT)L1623] is associated with a rapid lowering of systolic (top panels) and diastolic (bottom panels) arterial pressure as recorded during the first 30 minutes of intravenous delivery of the Ang-(1-12)-mAb. Values are means±SE; n=9 for females and n=9 for males.
Figure 5:
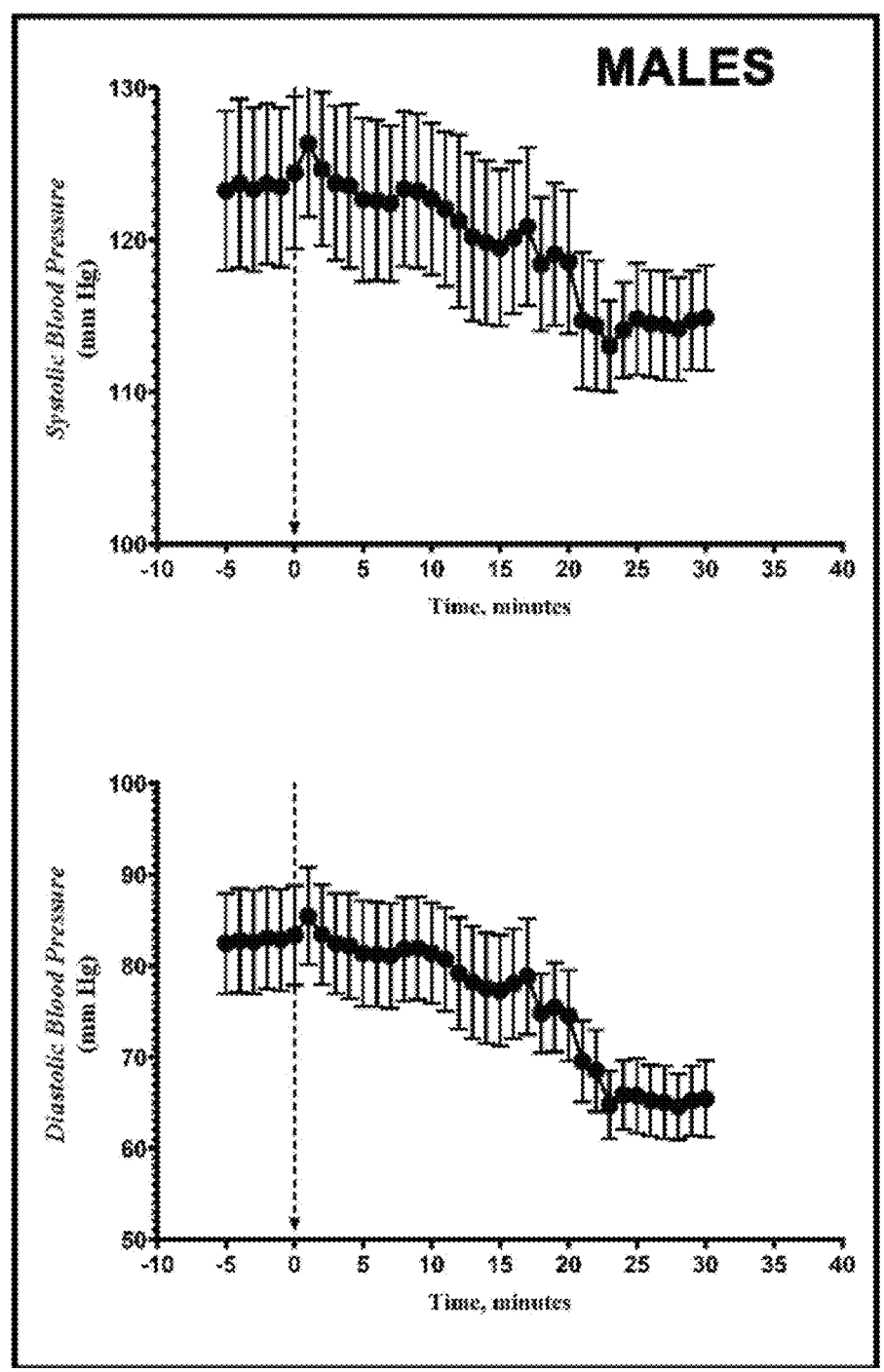

FIG. 5 documents the blood pressure response of female and male transgenic rats during the first 30 minutes following administration of the Ang-(1-12)-mAb. A clear and progressive decrease in systolic and diastolic blood pressure occurs in response to the delivery of the antibody in both female and male rats. This finding indicates an endogenous function of Ang-(1-12) as an Ang II forming substrate in anesthetized TGR(hAGT)L1623 rats that contributes to the maintenance of their resting blood pressure.

Figure 6:
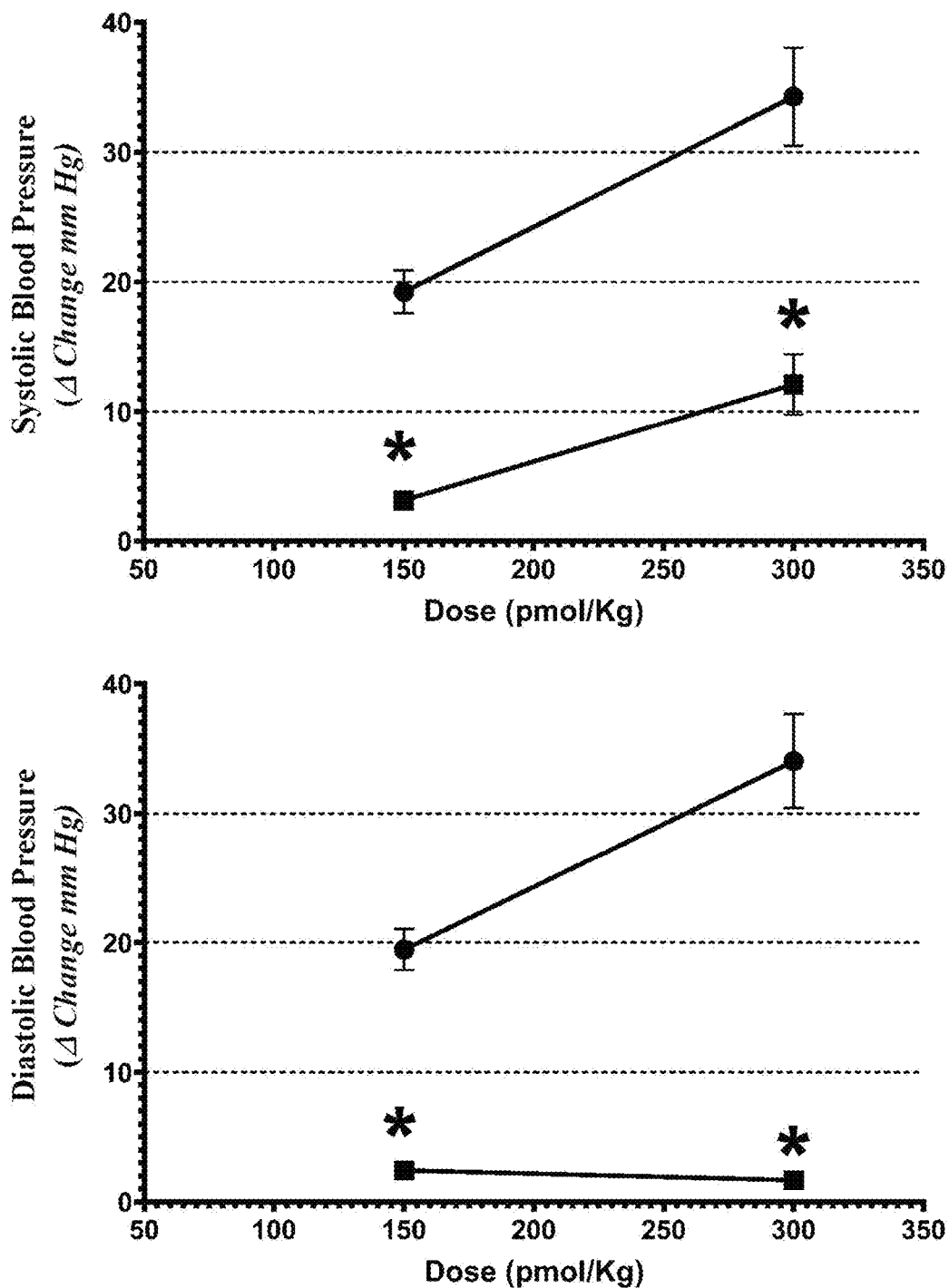
FIG. 6 shows data graphs indicating a sustained blockade of the pressor response due to intravenous Ang-(1-12) administration induced by the Ang-(1-12)-mAb in TGR (hAGT)L1623 rats during a 60 min post-injection period. Filled circles and solid lines are peak changes in systolic (top panel) and diastolic (bottom panel) blood pressure before (filled circles) and after h-Ang-(1-12) immunoneutralization (solid squares and solid lines). Value are means±SE (n=12 TGR(hAGT)L1623 rats injected with h-Ang-(1-12) at the dose of 150 pmol/Kg; n=7 TGR(hAGT)L1623 rats receiving 300 pmol/kg). Values are means±SE; *, $p<0.001$ compared with before administration of the Ang-(1-12)-mAb.

FIG. 6 shows that intravenous administration of the Ang-(1-12)-mAb elicited a sustained and complete blockade of the pressor activity of h-Ang-(1-12) lasting for up to 90 minutes as evidenced by the complete suppression of the Ang-(1-12) pressor response following repeated administration of bolus injections of h-Ang-(1-12) in TGR(hAGT) L1623 rats. The blockade of Ang-(1-12) pressor activity by the h-Ang-(1-12) mAb was equivalent in both male and female rats of each of the two tested strains. No attempt was made to test additional Ang-(1-12) responses beyond 90 minutes to comply with IACUC protocol considerations in anesthetized animals.

The specificity of Ang-(1-12) immune-neutralization was strengthened in parallel experiments that showed no differences in the magnitude of the peak mean arterial pressure response produced by bolus intravenous injections of Ang II (from a baseline of 95±6 mm Hg to a peak value of 114±8 mm Hg before compared to a baseline of 100±12 mm Hg to a peak value of 117±13 mm Hg 30-60 min after delivery of the Ang-(1-12) mAb; p>0.05). Injections of mouse pre-immune IgG did not significantly alter the magnitude of the pressor response to Ang-(1-12). In addition, the pressor response to injections of rat Ang-(1-12) were not modified by exposure to the h-Ang(1-12) mAb (data not shown).

Figure 7:
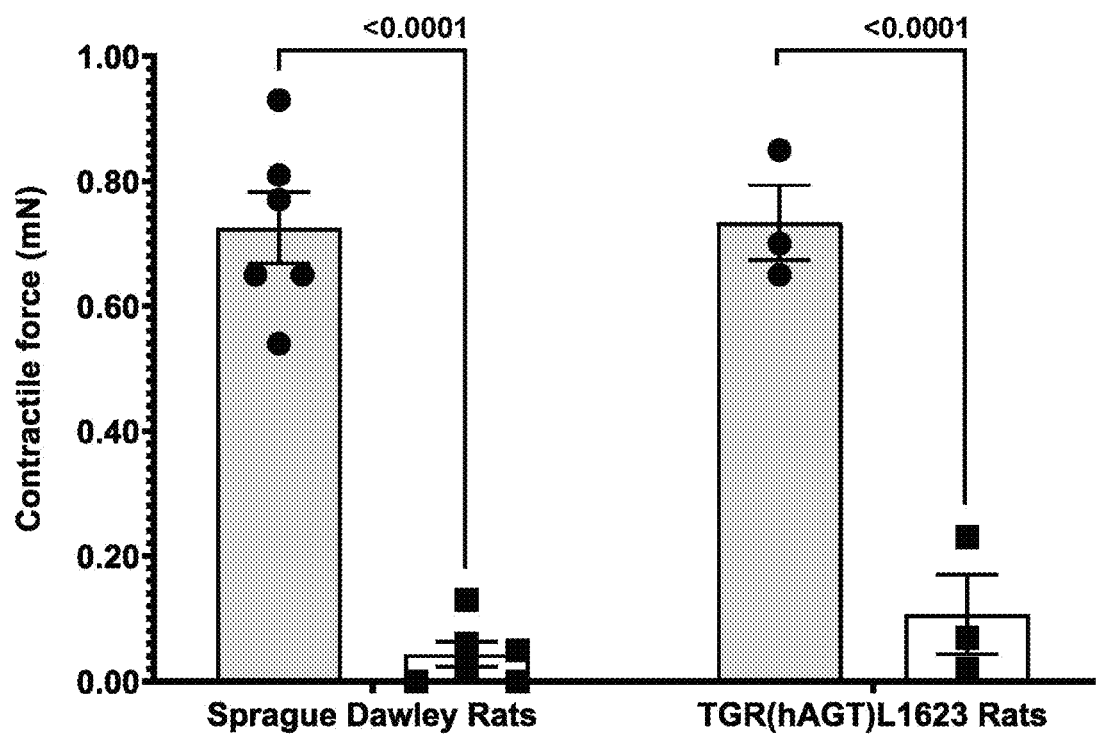
FIG. 7 shows a bar graph of contractile force indicating that h-Ang-(1-12) at a concentration of $5\times10^{-1}$ induces significant constrictor responses in carotid artery rings normalized for KCL from both SD and TGR(hAGT)L1623 rats. Treatment with the Ang-(1-12)-mAb produces an almost complete suppression of the constrictor response to the peptide that is sustained at or beyond 60 min following its delivery. Values are means±SE; n=6 SD rats and 3 TGR (hAGT)L1623 rats.

Ang-(1-12) Constrictor Activity in Isolated Carotid Artery Rings. To further ascertain the efficacy of the Ang-(1-12)-mAb in neutralizing the vasoconstrictor actions of the dodecapeptide, comparative studies were performed in the isolated carotid artery rings from SD (n=6) and TGR(hAGT) L1623 rats (n=3). As shown in FIG. 7, constrictor responses of carotid artery rings exposed to $5 \times 10^{-7}$ M Ang-(1-12) were equivalent in both SD and TGR(hAGT)L1623 rats. Rings superfusion with the Ang-(1-12)-mAb elicited an almost complete suppression of Ang-(1-12) constrictor activity that lasted for no less than 60 min following its administration. Incubation with non-immune mouse IgG had no effect on the Ang-(1-12) constrictor responses of carotid artery rings in either SD or TGR(hAGT)L1623 rats.

In this study, the first demonstration of the immunoneutralization capacity of a specific Ang-(1-12) mAb generated against the human sequence of this peptide strengthens the hypothesis that Ang-(1-12) is an endogenous substrate sourcing Ang II mechanisms of action. The ability of this mAb to fully neutralize the pressor activity of the human Ang-(1-12) was demonstrated in both SD rats and those expressing the human AGT gene. In both rat strains, the mAb prevented Ang-(1-12) from eliciting a hypertensive response for the entire duration of the study. The reduction in arterial pressure induced by the h-Ang-(1-12) mAb in rats expressing the human AGT gene in their genome uncovers for the first time that Ang-(1-12) may be contributing to maintain arterial pressure of TGR(hAGT)L1623 rats. A similar decrease in arterial pressure was not shown in SD rats nor did the h-Ang-(1-12) mAb mitigate the pressor responses induced by administration of the rat sequence of the Ang-(1-12) peptide. The absence of heart rate changes in response to endogenous neutralization of h-Ang-(1-12) pressor effects are in keeping with previous studies in Wistar rats[3], and in those in which a polyclonal antibody against the rat Ang-(1-12) amino acid sequence was given centrally for as long as 10 days of continuous administration.[24, 25] The further evaluation of the neutralizing ability of the mAb to block constrictor responses to Ang-(1-12) in isolated carotid arteries of both SD and TGR(hAGT)L1623 rats reinforced the specificity and potency of this mAb as a tool to unravel Ang-(1-12) contribution as a source for Ang II vasoconstrictor activity. The data obtained in the current study expands upon the previous demonstration of a sustained 10-day antihypertensive response induced by intracerebroventricular administration of a rat Ang-(1-12) polyclonal antibody in transgenic rats expressing the ren-2 gene [TGR(mRen2)27][24, 25].

Transgenic rats harboring the human AGT gene[26] emerge as a model of monogenetic hypertension in which hyperangiotensinemia, cardiac hypertrophy, and contractile dysfunction characterize the expression of human gene transcripts in the rat genome. Both human and rat renin hydrolytic activities are highly specific for their corresponding AGT substrates due to differences in the scissile bond between rat ($Leu^{10}$-$Leu^{11}$) and human ($Leu^{10}$-$Val^{11}$-) COOH-terminal sequences.[26, 27] The exclusion of rat renin as an Ang-(1-12) hydrolyzing enzyme has been confirmed in metabolism studies performed in the perfused hearts of normal and hypertensive rats[28] and the circulation of anephric rats.[29] The hypertension in TGR(hAGT)L1623 rats are associated with increased cardiac levels of Ang II[21] that courses with left ventricular dysfunction[30, 31] and desensitization of Ang II-mediated cardiac myocyte intracellular $K^+$-currents[32] and $Ca^{2+}$ mobilization.[22] Reversal of the hypertension by chronic administration of the Ang II receptor antagonist, valsartan confirms that the hypertension in TGR(hAGT)L1623 rats is dependent on a heightened state of Ang II expression and activity.[20] The characteristics of this model of humanized hypertension are now expanded by the current demonstration of a sexual dimorphism in terms of blood pressure but not heart rate in the anesthetized TGR(hAGT)L1623 rats. Future studies will reveal whether sex-differences differences in blood pressure were a product of anesthesia.

We confirmed that an injection of the h-Ang-(1-12) sequence induced pressor responses of similar magnitudes to those produced by rat Ang-(1-12) and equivalent to those originally reported in anesthetized Wistar rats and in isolated artery rings.[33] The absence of a substantial difference in the pressor response to the rat and human compositions reflects the fact that conversion of Ang-(1-12) into Ang I is primarily mediated by ACE in the circulation. The effects of the human Ang-(1-12) mAb were sustained for as long as 90 minutes as documented by the complete suppression of repeated injections of 300 pmol/kg of Ang-(1-12). The prolonged immunosuppression of the response to Ang-(1-12) in TGR(hAGT)L1623 rats were duplicated in the studies in which isolated carotid arteries from both SD and transgenic rats were used to test the inhibitory capacity of the mAb. The apparent prolonged inhibitory capacity of the h-Ang-(1-12) mAb is in keeping with other pharmacokinetic data for marketed mABs where the IgG1 and IgG2 isotype antibody half-lives ranged from 6 to 21 days.[35-38]

As early as 1983 Dzau and colleagues[39] discussed the potential superiority of antibodies and Fab fragments over pharmacological inhibitors as therapeutic agents. Today, humanized mAbs, having achieved center stage in the treatment of human diseases, are expected to generate revenues of $300 billion by 2025.[40] As reviewed by Mak and Saunders,[41] the advantages of these antibodies over mouse mAb include: a)—reduced immunogenicity; b)—the presence of the C region allowing for human effector functions to take place; and c)—a significant increase in serum half-life of the mAb in humans. Monoclonal antibodies directed to different epitopes on the ACE molecule have shed light into the role of the N- and C-domain of the enzyme[42] while mAbs directed against Ang II confirmed its hypertensive role in experimental renal hypertension.[43] We used a mAb against Ang-(1-7) to uncover the robust antihypertensive action of endogenous Ang-(1-7) during a fortnight therapy with lisinopril or losartan[44] or after chronic salt depletion in SHR.[45] The tempo for introducing newer molecular tools to treat vascular disease is maturing based on the demonstration of a potential for Ang II vaccines to treat hypertension[46-48] or prevent progression of abdominal aortic aneurysms in rats.[49]

Recently, a liver-targeted, stable antisense oligonucleotides (ASO), 15, 18, 50 a Crispr-Cas9 mediated disruption of AGT,[51] and a small interfering RNA (siRNA)[14] targeting AGT are described as new frontiers in the therapy of resistant hypertension. The budding clinical viability of these approaches is documented in a poster presented at the 2020 scientific meeting of the AHA. At this virtual meeting of the AHA, Huang et al.[13] showed that a 12-week dose-related reduction in serum AGT levels was accompanied by an over 10 mm Hg reduction of mean 24-hour systolic blood pressure at week 8 following single doses of 100 mg or 200 mg of the hepatic RNAi. The fact that these gene suppressing approaches require greater than 95% suppression of the hepatic AGT to achieve a large reduction in plasma Ang II concentrations needs to be carefully considered as new evidence demonstrates that *"AGT exerts effects beyond being a sole provider of angiotensin peptides."*[16] The multifaceted functions of the serpin sequence of human AGT [des-(Ang I)AGT] include acting as an antiangiogenic factor,[52, 53] an inhibitor of VEGF-induced endothelial cell migration,[53] a modulator of blood-brain barrier permeability,[54] and diet-induced obesity and liver steatosis.[55]

The results obtained in the current report in an experimental model of hypertension due to increased Ang II production from the human AGT gene[20-22] and those obtained in rats with TGR(mRen2)27 hypertension[24, 25] confirms that a noncanonical pathway through Ang-(1-12) processing is an endogenous source for Ang II actions. We advance the hypothesis that targeting Ang-(1-12) suppression with mAbs may constitute a selective approach to suppressing Ang II formation without interfering with des-(Ang I)AGT expression and functions. The utility of h-Ang-(1-12) mAbs may extend to preventing the pathological consequences of increased plasma and myocardial Ang II in the evolution of SARS-CoV-2 infection[56, 57] and the plasma Ang-(1-12) elevations in non-surviving patients with a diagnosis of the Acute Respiratory Distress Syndrome.[58] The studies reported here constitute the basis for the further pursuit of these ideas by demonstrating the feasibility of sustained suppression of Ang II mechanisms of action through immunoneutralization of Ang-(1-12) in rats with human AGT-dependent hypertension and patients with conditions of increased plasma/tissue Ang II.

Suboptimal blood pressure control constitutes a leading risk factor for cardiovascular disease and a leading worldwide cause of disability-adjusted life years. Emerging efforts to discover new therapies that reduce pill-burden, enhance blood pressure control and adherence to therapy are beginning to emerge by targeting expression of hepatic AGT, the only known protein from which angiotensins are generated. The relative recent identification of Ang-(1-12) as an alternate endogenous Ang II-forming substrate created the possibility to explore immunoneutralization of this peptide as a means to circumvent the potential risks that are associated with complete suppression of hepatic AGT from which only the first 10 amino acids of the 425 components of the human sequence comprise the peptide from which the angiotensins are generated. In the pursuit of this longer-term goal we generated Ang-(1-12) mAbs directed against the human sequence of the AGT protein and documented its potency in suppressing the vasoconstrictor response to the intravenous administration of the peptide in rats with and without endogenous expression of the human AGT gene and isolated carotid artery strips. The ability of this h-Ang-(1-12) mAb to completely suppress Ang-(1-12) vasoconstrictor activity in a dose-dependent manner and to uncover a vasodilator response following its administration lasting for the duration of the study agrees with the concept that Ang-(1-12) is an endogenously functional Ang II-forming substrate and that its neutralization may provide an alternate and safer mechanism of action that avoids a need to essentially suppress hepatic AGT synthesis to zero.

REFERENCES

1. Ferrario C M. New physiological concepts of the renin-angiotensin system from the investigation of precursors and products of angiotensin i metabolism. Hypertension. 2010; 55:445-452
2. Ferrario C M, Ahmad S, Varagic J, Cheng C P, Groban L, Wang H, Collawn J F, Dell Italia L J. Intracrine angiotensin ii functions originate from noncanonical pathways in the human heart. Am J Physiol Heart Circ Physiol. 2016; 311:H404-414
3. Nagata S, Kato J, Sasaki K, Minamino N, Eto T, Kitamura K. Isolation and identification of proangiotensin-12, a possible component of the renin-angiotensin system. Biochem Biophys Res Commun. 2006; 350:1026-1031
4. Prosser H C, Forster M E, Richards A M, Pemberton C J. Cardiac chymase converts rat proangiotensin-12 (pa12) to angiotensin ii: Effects of pa12 upon cardiac haemodynamics. Cardiovasc Res. 2009; 82:40-50
5. Ahmad S, Simmons T, Varagic J, Moniwa N, Chappell M C, Ferrario C M. Chymase-dependent generation of angiotensin ii from angiotensin-(1-12) in human atrial tissue. PLoS One. 2011; 6:e28501
6. Ahmad S, Varagic J, Groban L, Dell'Italia L J, Nagata S, Kon N D, Ferrario C M. Angiotensin-(1-12): A chymase-mediated cellular angiotensin ii substrate. Curr Hypertens Rep. 2014; 16:429
7. Ahmad S, Varagic J, VonCannon J L, Groban L, Collawn J F, Dell'Italia L J, Ferrario C M. Primacy of cardiac chymase over angiotensin converting enzyme as an angiotensin-(1-12) metabolizing enzyme. Biochem Biophys Res Commun. 2016; 478:559-564
8. Ahmad S, Wei C C, Tallaj J, Dell'Italia L J, Moniwa N, Varagic J, Ferrario C M. Chymase mediates angiotensin-(1-12) metabolism in normal human hearts. J Am Soc Hypertens. 2013; 7:128-136
9. Ali W, Bakris G. The management of hypertension in 2018: What should the targets be? Curr Hypertens Rep. 2019; 21:41
10. Carey R M, Calhoun D A, Bakris G L, Brook R D, Daugherty S L, Dennison-Himmelfarb C R, Egan B M, Flack J M, Gidding S S, Judd E, Lackland D T, Laffer C L, Newton-Cheh C, Smith S M, Taler S J, Textor S C, Turan T N, White W B, American Heart Association Professional/Public E, Publications Committee of the Council on H, Council on C, Stroke N, Council on Clinical C, Council on G, Precision M, Council on Peripheral Vascular D, Council on Quality of C, Outcomes R, Stroke C. Resistant hypertension: Detection, evaluation, and management: A scientific statement from the american heart association. Hypertension. 2018; 72:e53-e90
11. Dusing R. Mega clinical trials which have shaped the ras intervention clinical practice. Ther Adv Cardiovasc Dis. 2016; 10:133-150
12. Reyes S, Varagic J, Ahmad S, VonCannon J, Kon N D, Wang H, Groban L, Cheng C P, Dell'Italia L J, Ferrario C M. Novel cardiac intracrine mechanisms based on ang-(1-12)/chymase axis require a revision of therapeutic approaches in human heart disease. Curr Hypertens Rep. 2017; 19:16
13. Huang S A, Taubel J, Fiore G, Dewland P, Bakris G L, Desai A S, Cheng Y, Agarwal S, Harrop J, Nguyen H V, Lu J, Foster D, Vaishnaw A, Kim J B. Abstract 14387: Dose-related reductions in blood pressure with a rna interference (rnai) therapeutic targeting angiotensinogen in hypertensive patients: Interim results from a first-in-human phase 1 study of aln-agt01. Circulation. 2020; 142:A14387-A14387
14. Uijl E, Mirabito Colafella K M, Sun Y, Ren L, van Veghel R, Garrelds I M, de Vries R, Poglitsch M, Zlatev I, Kim J B, Hoorn E J, Foster D, Danser A H J. Strong and sustained antihypertensive effect of small interfering rna targeting liver angiotensinogen. Hypertension. 2019; 73:1249-1257
15. Mullick A E, Yeh S T, Graham M J, Engelhardt J A, Prakash T P, Crooke R M. Blood pressure lowering and safety improvements with liver angiotensinogen inhibition in models of hypertension and kidney injury. Hypertension. 2017; 70:566-576
16. Lu H, Cassis L A, Kooi C W, Daugherty A. Structure and functions of angiotensinogen. Hypertens Res. 2016; 39:492-500
17. Lu H, Wu C, Howatt D A, Balakrishnan A, Moorleghen J J, Chen X, Zhao M, Graham M J, Mullick A E, Crooke R M, Feldman D L, Cassis L A, Vander Kooi C W, Daugherty A. Angiotensinogen exerts effects independent of angiotensin ii. Arterioscler Thromb Vasc Biol. 2016; 36:256-265
18. Wu C H, Wang Y, Ma M, Mullick A E, Crooke R M, Graham M J, Daugherty A, Lu H S. Antisense oligonucleotides targeting angiotensinogen: Insights from animal studies. Biosci Rep. 2019; 39
19. Ye F, Wang Y, Wu C, Howatt D A, Wu C H, Balakrishnan A, Mullick A E, Graham M J, Danser A H J, Wang J, Daugherty A, Lu H S. Angiotensinogen and megalin interactions contribute to atherosclerosis-brief report. Arterioscler Thromb Vasc Biol. 2019; 39:150-155
20. Ferrario C M, VonCannon J, Ahmad S, Wright K N, Roberts D J, Wang H, Yamashita T, Groban L, Cheng C P, Collawn J F, Dell'Italia L J, Varagic J. Activation of the human angiotensin-(1-12)-chymase pathway in rats with human angiotensinogen gene transcripts. Front Cardiovasc Med. 2019; 6:163
21. Ferrario C M, VonCannon J, Jiao Y, Ahmad S, Bader M, Dell'Italia L J, Groban L, Varagic J. Cardiac angiotensin-(1-12) expression and systemic hypertension in rats expressing the human angiotensinogen gene. Am J Physiol Heart Circ Physiol. 2016; 310:H995-1002
22. Reyes S, Cheng C P, Roberts D J, Yamashita T, Ahmad S, VonCannon J L, Wright K N, Dell'Italia L J, Varagic J, Ferrario C M. Angiotensin-(1-12)/chymase axis modulates cardiomyocyte 1-type calcium currents in rats expressing human angiotensinogen. Int J Cardiol. 2019; 297:104-110

23. Percie du Sert N, Hurst V, Ahluwalia A, Alam S, Avey M T, Baker M, Browne W J, Clark A, Cuthill I C, Dirnagl U, Emerson M, Garner P, Holgate S T, Howells D W, Karp N A, Lazic S E, Lidster K, MacCallum C J, Macleod M, Pearl E J, Petersen O H, Rawle F, Reynolds P, Rooney K, Sena E S, Silberberg S D, Steckler T, Wurbel H. The arrive guidelines 2.0: Updated guidelines for reporting animal research. PLoS Biol. 2020; 18:e3000410
24. Isa K, Garcia-Espinosa M A, Arnold A C, Pirro N T, Tommasi E N, Chappel M C, Ferrario C M, Diz D I. Angiotensin-(1-12) contributes to renin-independent angiotensin ii activity in brain [online]. HYPERTENSION. 2018; 52
25. Isa K, Garcia-Espinosa M A, Arnold A C, Pirro N T, Tommasi E N, Ganten D, Chappell M C, Ferrario C M, Diz D I. Chronic immunoneutralization of brain angiotensin-(1-12) lowers blood pressure in transgenic (mren2) 27 hypertensive rats. Am J Physiol Regul Integr Comp Physiol. 2009; 297:R111-115
26. Ganten D, Wagner J, Zeh K, Bader M, Michel J B, Paul M, Zimmermann F, Ruf P, Hilgenfeldt U, Ganten U, et al. Species specificity of renin kinetics in transgenic rats harboring the human renin and angiotensinogen genes. Proc Natl Acad Sci USA. 1992; 89:7806-7810
27. Yan Y, Zhou A, Carrell R W, Read R J. Structural basis for the specificity of renin-mediated angiotensinogen cleavage. J Biol Chem. 2019; 294:2353-2364
28. Trask A J, Jessup J A, Chappell M C, Ferrario C M. Angiotensin-(1-12) is an alternate substrate for angiotensin peptide production in the heart. Am J Physiol Heart Circ Physiol. 2008; 294:H2242-2247
29. Ferrario C M, Varagic J, Habibi J, Nagata S, Kato J, Chappell M C, Trask A J, Kitamura K, Whaley-Connell A, Sowers J R. Differential regulation of angiotensin-(1-12) in plasma and cardiac tissue in response to bilateral nephrectomy. Am J Physiol Heart Circ Physiol. 2009; 296:H1184-1192
30. Li T, Zhang X, Cheng H J, Zhang Z, Ahmad S, Varagic J, Li W, Cheng C P, Ferrario C M. Critical role of the chymase/angiotensin-(1-12) axis in modulating cardiomyocyte contractility. Int J Cardiol. 2018; 264:137-144
32. De Mello W C, Dell'Itallia L J, Varagic J, Ferrario C M. Intracellular angiotensin-(1-12) changes the electrical properties of intact cardiac muscle. Mol Cell Biochem. 2016; 422:31-40
33. Prosser H C, Richards A M, Forster M E, Pemberton C J. Regional vascular response to proangiotensin-12 (pa12) through the rat arterial system. Peptides. 2010; 31:1540-1545
34. Moniwa N, Varagic J, Simington S W, Ahmad S, Nagata S, Voncannon J L, Ferrario C M. Primacy of angiotensin converting enzyme in angiotensin-(1-12) metabolism. Am J Physiol Heart Circ Physiol. 2013; 305:H644-650
35. Lin Y S, Nguyen C, Mendoza J L, Escandon E, Fei D, Meng Y G, Modi N B. Preclinical pharmacokinetics, interspecies scaling, and tissue distribution of a humanized monoclonal antibody against vascular endothelial growth factor. J Pharmacol Exp Ther. 1999; 288:371-378
36. Lobo E D, Hansen R J, Balthasar J P. Antibody pharmacokinetics and pharmacodynamics. J Pharm Sci. 2004; 93:2645-2668
37. Ovacik M, Lin K. Tutorial on monoclonal antibody pharmacokinetics and its considerations in early development. Clin Transl Sci. 2018; 11:540-552
38. Walker K W, Salimi-Moosavi H, Arnold G E, Chen Q, Soto M, Jacobsen F W, Hui J. Pharmacokinetic comparison of a diverse panel of non-targeting human antibodies as matched igg1 and igg2 isotypes in rodents and non-human primates. PLoS One. 2019; 14:e0217061
39. Dzau V J, Devine D, Mudgett-Hunter M, Kopelman R I, Barger A C, Haber E. Antibodies as specific renin inhibitors: Studies with polyclonal and monoclonal antibodies and fab fragments. Clin Exp Hypertens A. 1983; 5:1207-1220
40. Lu R M, Hwang Y C, Liu I J, Lee C C, Tsai H Z, Li H J, Wu H C. Development of therapeutic antibodies for the treatment of diseases. J Biomed Sci. 2020; 27:1
41. Mak T W, Saunders M E. 7—exploiting antigen-antibody interaction. In: Mak T W, Saunders M E, eds. The immune response. Burlington: Academic Press; 2006: 147-177.
42. Balyasnikova I V, Skirgello O E, Binevski P V, Nesterovitch A B, Albrecht R F, 2nd, Kost O A, Danilov S M. Monoclonal antibodies 1g12 and 6a12 to the n-domain of human angiotensin-converting enzyme: Fine epitope mapping and antibody-based detection of ace inhibitors in human blood. J Proteome Res. 2007; 6:1580-1594
43. Reilly T M, Wong P C, Price W A, Timmermans P B. Characterization of the functional antagonism and antihypertensive activity displayed by a monoclonal antibody to angiotensin ii. J Pharmacol Exp Ther. 1988; 244:160-165
44. Iyer S N, Chappell M C, Averill D B, Diz D I, Ferrario C M. Vasodepressor actions of angiotensin-(1-7) unmasked during combined treatment with lisinopril and losartan. Hypertension. 1998; 31:699-705
45. Iyer S N, Averill D B, Chappell M C, Yamada K, Allred A J, Ferrario C M. Contribution of angiotensin-(1-7) to blood pressure regulation in salt-depleted hypertensive rats. Hypertension. 2000; 36:417-422
46. Chen X, Qiu Z, Yang S, Ding D, Chen F, Zhou Y, Wang M, Lin J, Yu X, Zhou Z, Liao Y. Effectiveness and safety of a therapeutic vaccine against angiotensin ii receptor type 1 in hypertensive animals. Hypertension. 2013; 61:408-416
47. Ding D, Du Y, Qiu Z, Yan S, Chen F, Wang M, Yang S, Zhou Y, Hu X, Deng Y, Wang S, Wang L, Zhang H, Wu H, Yu X, Zhou Z, Liao Y, Chen X. Vaccination against type 1 angiotensin receptor prevents streptozotocin-induced diabetic nephropathy. J Mol Med (Berl). 2016; 94:207-218
48. Garay-Gutierrez N F, Hernandez-Fuentes C P, Garcia-Rivas G, Lavandero S, Guerrero-Beltran C E. Vaccines against components of the renin-angiotensin system. Heart Fail Rev. 2020
49. Kurashiki T, Miyake T, Nakagami H, Nishimura M, Morishita R. Prevention of progression of aortic aneurysm by peptide vaccine against ang ii (angiotensin ii) in a rat model. Hypertension. 2020; 76:1879-1888
50. Ravichandran K, Ozkok A, Wang Q, Mullick A E, Edelstein C L. Antisense-mediated angiotensinogen inhibition slows polycystic kidney disease in mice with a targeted mutation in pkd2. Am J Physiol Renal Physiol. 2015; 308:F349-357
51. Sun H, Hodgkinson C, Pratt R E, Dzau V J. Abstract 15555: Potential cure for hypertension? The effect of crispr genome editing. Circulation. 2020; 142:A15555-A15555
52. Celerier J, Cruz A, Lamande N, Gasc J M, Corvol P. Angiotensinogen and its cleaved derivatives inhibit angiogenesis. Hypertension. 2002; 39:224-228
53. Corvol P, Lamande N, Cruz A, Celerier J, Gasc J M. Inhibition of angiogenesis: A new function for angiotensinogen and des(angiotensin i)angiotensinogen. Curr Hypertens Rep. 2003; 5:149-154
54. Morimoto S, Cassell M D, Beltz T G, Johnson A K, Davisson R L, Sigmund C D. Elevated blood pressure in transgenic mice with brain-specific expression of human angiotensinogen driven by the glial fibrillary acidic protein promoter. Circ Res. 2001; 89:365-372
55. Wu C, Xu Y, Lu H, Howatt D A, Balakrishnan A, Moorleghen J J, Vander Kooi C W, Cassis L A, Wang J A, Daugherty A. Cys18-cys137 disulfide bond in mouse angiotensinogen does not affect angii-dependent functions in vivo. Hypertension. 2015; 65:800-805
56. Wu C, Ye D, Mullick A E, Li Z, Danser A H J, Daugherty A, Lu H S. Effects of renin-angiotensin inhibition on ace2 and tmprss2 expression: Insights into covid-19. bioRxiv. 2020
57. Wu Z, Hu R, Zhang C, Ren W, Yu A, Zhou X. Elevation of plasma angiotensin ii level is a potential pathogenesis for the critically ill covid-19 patients. Crit Care. 2020; 24:290
58. Reddy R, Asante I, Liu S, Parikh P, Liebler J, Borok Z, Rodgers K, Baydur A, Louie S G. Circulating angiotensin peptides levels in acute respiratory distress syndrome correlate with clinical outcomes: A pilot study. PLoS One. 2019; 14:e0213096

Example 3

Methods and Data Supplement for Examples 1 and 2

Angiotensin-(1-12) Monoclonal Antibody: A custom-made monoclonal antibody directed to the C-terminus of the human Ang-(1-12) [h-Ang-(1-12)] peptide sequence [DRVYIHPFHLVI (SEQ ID NO:9)] (purity>98%) was developed in collaboration with GenScript Biotech., Piscataway, NJ using a standard protocol. First, h-Ang-(1-12) polyclonal antibodies were obtained by immunizing 5 BALB/c mice with an Ang-(1-12)-keyhole limpet hemocyanin conjugated to the N-terminus. Screening of immunized BALB/c mouse antiserum by a radioimmunoassay (RIA) using highly purified radiolabeled h-Ang-(1-12) [$^{125}$I-hAng-(1-12), purity>99%, specific activity 3,900 cpm/fmol] showed excellent specificity for h-Ang-(1-12) ($EC_{50}$ range: 13-208 fmol) and less than 0.001% cross-reactivity with human AGT protein or AGT-derived angiotensin peptides [Ang I, Ang II and Ang-(1-7)]. Mouse splenocytes were then fused with Sp2/0-Ag14 myeloma cells (American Tissue Type Culture). After two rounds of cell fusion, several hybridoma clones were selected, cultured and antibodies from cells' supernatant were screened. The monoclonal antibody (mAb) producing hybridoma cells showed excellent specificity for hAng-(1-12) ($EC_{50}$ range: 67-123 fmol). The stable clone (14B3) of hybridoma cells were cultured and the purified IgG mAbs were used in this study.

The hybridoma cells (Clone 14B3) were grown for 3-4 days in Dulbecco's Modified Eagle Medium (DMEM) culture media supplemented with 2% FBS (Fetal bovine serum) and 2 mM L-glutamine. The conditioned culture supernatants were collected by centrifuging sequentially at 200 g for 3 min to remove the cells and then at 18,000 g for 30 min to remove the cell debris. The mAb IgG was purified from the clear supernatant using a Protein L agarose resin column (Thermo Fisher Scientific). The Protein L purified mAb IgG was further concentrated using a special ultrafiltration unit (Amicon Ultra-15 centrifugal filter device) according to manufacturer's directions. The concentrated mAb IgG was washed three times with PBS and tested by RIA for h-Ang-(1-12) specificity and cross-reactivity before using it in the immunoneutralization study. To test the stability of the Protein L purified mAB, we incubated the purified mAb (concentration 2 mg/mL) with human transgenic rat's serum) for up to 7 days at 37° C. At the end of the 7 days of incubation period, a highly purified radiolabeled $^{125}$I-h-Ang-(1-12) substrate [~50 fmoles/200 µL reaction, specific activity 3,900 cpm/fmol, purity≥99%] and recombinant human chymase (0.325 µg/mL Sigma-Aldrich, St. Louis, MO) were added and incubated at 37° C. for an additional 1 hr. At the end of incubation, the Ang II product formation and h-Ang-(1-12) substrate were separated on C18 column by HPLC, as previously described by us elsewhere.[1, 2]

h-Ang-(1-12) Specificity and Cross-reactivity Assays: For specificity, a synthetic non-radiolabeled h-Ang-(1-12) standard (purity≥98%) was used. Briefly, 200 µL of the RIA buffer (50 mM PBS, 25 mM EDTA, 0.5% triton X-100, 0.05% sodium azide and 0.5% BSA, pH 7.4) containing 50 µL of mAb (1:2,000 dilution of IgG concentration 1.3 mg/mL), 50 µL of 125I-Ang-(1-12) [6-8 fmoles/tube, purity>99%] and 50 µL of different concentrations of non-radiolabeled human Ang-(1-12) peptide (0 to 10,000 fmol/0.2 mL RIA tube) were combined and the RIA tubes were incubated overnight for 20-22 hours at 4° C. At the end of incubation period, 50 µL of 1% γ-globulin were added, mixed, and the bound/free (B/Bo) forms of h-Ang-(1-12) were then separated by precipitating the bound (B) fraction with 200 µL of 23% polyethylene glycol (PEG). The bound and unbound (Bo) traces were separated by centrifuging the tubes at 3,000 rpm for 30 min at 4° C. The radioactivity corresponding to the antibody-bound antigen in the precipitate were measured in a PerkinElmer Wizard2 Gamma Counter. The binding data were analyzed and graphed using a statistical program (GraphPad Prism 8). To examine the cross-reactivity of the mAb with human and rat AGT or AGT-derived angiotensin peptides, several fold higher concentrations (AGT up to 10,000 fmol and angiotensin peptides up to 5,000 fmol) were used. Briefly, in a total of 200 µL of RIA buffer we added 50 µL of h-Ang-(1-12) mAb (1:2,000 dilution), 50 µL of $^{125}$I-Ang-(1-12) and 50 µL of non-radiolabeled angiotensin peptides [Ang I, (DRVYIHPFHL; SEQ ID NO:20); Ang-(1-9), (DRVYIHPFH; SEQ ID NO:23); Ang II, (DRVYIHPF; SEQ ID NO:21); Ang-(1-7), (DRVYIHP; SEQ ID NO:22) and rat Ang-(1-12), (DRVYIHPFHLLY; SEQ ID NO:24)] or purified AGT protein (10,000 fmol per RIA tube) and after mixing the contents, the RIA tubes were incubated overnight (20-22 hours at 4° C.) and processed as described above.

Efficacy of Ang-(1-12) Immunoneutralization in vivo: We examined the systemic vasoconstrictor activity of Ang-(1-12) (dose range 75-300 pmol) in 20 (10 females) Sprague Dawley (SD) rats (age 12-weeks) and 20 (10 female) other rats expressing the human sequence of the AGT gene [TGR(hAGT)L1623] (age 10-12 weeks) following induction of general anesthesia with thio-butabarbital sodium [Inactin® (135 mg/kg, i.p.)] and tracheal intubation for mechanical ventilation. Plastic catheters were introduced into a left carotid artery [PE-50 catheter attached to a heparinized saline wash syringe (15 USP U/mL) and a femoral vein (PE-10) for drug delivery. Phasic and mean arterial pressures, recorded with a True Wave pressure transducer (Edwards Lifesciences, Co, Irvine, CA) connected to the arterial cannula, were processed by a data-acquisition and analysis system with Acknowledge 5 software (MP160, BIOPAC System Inc., Goleta, CA). Heart rate was derived by the software from the electrical analysis of the rise portion of the pressure waveform.

In a separate group of 12 TGR(hAGT)L1623 rats (6 females) the blood pressure and heart rate responses to intravenous bolus injection of a monoclonal antibody directed against the human amino acid sequence of Ang-(1-12) [Ang-(1-12)-mAb] was administered at a dose of 30 mg/kg. This dose was demonstrated in pilot experiments to achieve a maximal reduction in the Ang-(1-12) pressor response at doses equal to or higher than 300 pmol/kg in 100 µL saline. The Ang-(1-12)-mAb was diluted in physiological saline to a concentration of 30 mg in a volume not to exceed 1 mL of buffered saline. The specificity of the immunoneutralization of Ang-(1-12) was evaluated in additional experiments in which the rat sequence of Ang-(1-12) (300 pmol/kg, n=2); Ang II (50 pmol/kg; n=3 TGR(hAGT)L1623 rats) or an immune mouse IgG (30 mg/kg, n=4 TGR(hAGT)L1623 rats; Innovative Research, Inc. Novi, MI) were administered intravenously.

Efficacy of Ang-(1-12) Immunoneutralization in Isolated Carotid Arteries. The ability of the Ang-(1-12)-mAb to block mouse IgG (2.3 mg/mL). In all cases, each treatment was run in quadruplicate and the average response used for analysis.

REFERENCES

1. Ahmad S, Varagic J, VonCannon J L, Groban L, Collawn J F, Dell'Italia L J, Ferrario C M. Primacy of cardiac chymase over angiotensin converting enzyme as an angiotensin-(1-12) metabolizing enzyme. Biochem Biophys Res Commun. 2016; 478:559-564
2. Ahmad S, Wright K N, Sun X, Groban L, Ferrario C M. Mast cell peptidases (carboxypeptidase a and chymase)-mediated hydrolysis of human angiotensin-(1-12) substrate. Biochem Biophys Res Commun. 2019; 518:651-656
3. Lee J H, Zhang J, Massmann G A, Figueroa J P. Antenatal betamethasone increases vascular reactivity to endothelin-1 by upregulation of cd38/cadpr signaling. J Dev Orig Health Dis. 2014; 5:56-62

TABLE 1

| | | | IMGT Analysis of V(D)J Junctions | | | | |
|---|---|---|---|---|---|---|---|
| Sequence | V-GENE and allele | Functionality | V-region % identity (nt) | J-GENE and allele | D-GENE and allele | AA Junction | Junction frame |
| $V_H$ | Musmus IGHV3-2*02 F | productive | 97.57% (281/288 nt) | Musmus IGHJ2*01 F | Musmus IGHD2-3 *01 F | CARGSY YFDYW (SEQ ID NO: 1) | in-frame |
| $V_L$ | Musmus IGKV8-21*01 F | productive | 100.00% (297/297 nt) | Musmus IGKJ1*01 F | — | CKQSYN LRTF (SEQ ID NO: 2) | in-frame |

Ang-(1-12) vasoconstrictor activity in 6 SD and 3 TGR (hAGT)L1623 rats was further assessed in isolated carotid artery rings that were mounted in organ chambers as described elsewhere.[3] Under a dissecting microscope, both carotid arteries were dissected free of adventitial tissue, cut into 1.5-2 mm segments and mounted on a myograph (Multi Myograph, Model 610M Danish Myo Technologies, Aarhus, Denmark) using two stainless steel hooks. In all the arterial segments, the endothelium was disrupted by passing a human hair through the lumen of the vessel. The myograph chamber was filled with Krebs-Henseleit buffer (KHB) solution, maintained at 37° C. and aerated with 95% O2/5% CO2. The vessels were washed and incubated for 30 min before determining the optimal diameter. Each arterial segment was stretched to its individual optimal lumen diameter following the normalization procedure previously described. In all studies, after obtaining the optimal diameter, a 30-min equilibration period preceded the addition of the test substances. Contractile responses to a single dose of 62.5 mM KCl was obtained for all segments by calculating the average of three consecutive doses tested at 15 min intervals. This response was used to normalize tension between individual arterial segments. A single dose of $5 \times 10^{-7}$ M Ang-(1-12) was used to evaluate contractile response to avoid desensitization to the effects of Ang-(1-12). In parallel experiments, arterial segments were preincubated for 60 min with either the Ang-(1-12)-mAb antibody or non-immune

TABLE 2

SEX DIFFERENCES IN THE BASELINE HEMODYNAMICS

| | Sprague Dawley Rats | |
|---|---|---|
| VARIABLE | Males | Females |
| Systolic Blood Pressure, mm Hg | 135 ± 2 | 117 ± 2<br>p < 0.001 |
| Diastolic Blood Pressure, mm Hg | 85 ± 2 | 70 ± 2<br>p < 0.001 |
| Mean Blood Pressure, mm Hg | 105 ± 2 | 92 ± 2<br>p < 0.001 |
| Heart Rate, mm Hg | 328 ± 4 | 308 ± 5<br>p < 0.001 |
| | TGR(hAGT)L1623 Rats | |
| | Males | Females |
| Systolic Blood Pressure, mm Hg | 134 ± 2 | 126 ± 2<br>p = 0.007 |
| Diastolic Blood Pressure, mm Hg | 93 ± 3 | 91 ± 4<br>p n.s. |
| Mean Blood Pressure, mm Hg | 113 ± 2 | 102 ± 3<br>p = 0.001 |
| Heart Rate, mm Hg | 312 ± 4 | 316 ± 6<br>n.s. |

Values are means ± SE.
p values compared to Sprague Dawley; n.s., p > 0.05

That which is claimed is:

1. A monoclonal antibody or a fragment thereof, wherein the monoclonal antibody or the fragment thereof binds to human angiotensin-(1-12) and comprises a light chain variable region having SEQ ID NO:3 (LC CDR1), SEQ ID NO:4 (LC CDR2) and SEQ ID NO:5 (LC CDR3) and comprises a heavy chain variable region having SEQ ID NO:6 (HC CDR1), SEQ ID NO:7 (HC CDR2), and SEQ ID NO:8 (HC CDR3).

2. The monoclonal antibody or the fragment thereof of claim 1, wherein the heavy chain variable region comprises an amino acid sequence having at least about 70% sequence identity to SEQ ID NO:10.

3. The monoclonal antibody or the fragment thereof of claim 1, wherein the light chain variable region comprises an amino acid sequence having at least about 70% sequence identity to SEQ ID NO:11.

4. The monoclonal antibody or the fragment thereof of claim 1, wherein the monoclonal antibody or the fragment thereof is configured for intracellular delivery.

5. The monoclonal antibody or the fragment thereof of claim 4, wherein the monoclonal antibody or the fragment thereof is configured for intracellular delivery as a liposomal formulation.

6. The monoclonal antibody or the fragment thereof of claim 1, wherein the monoclonal antibody or the fragment thereof reduces, inhibits, or blocks one or more angiotensin II pathological mechanisms and/or actions.

7. A pharmaceutical composition comprising the monoclonal antibody or the fragment thereof of claim 1 and a pharmaceutically acceptable carrier.

8. A method of reducing or inhibiting pressor activity of angiotensin-(1-12) in a subject, the method comprising administering a therapeutically effective amount of the monoclonal antibody or the fragment thereof of claim 1 to a subject, thereby reducing or inhibiting pressor activity of angiotensin-(1-12) in the subject.

9. A method of treating hypertension in a subject, the method comprising administering to the subject a therapeutically effective amount of the monoclonal antibody or the fragment thereof of claim 1, thereby treating the hypertension in the subject.

10. The monoclonal antibody or the fragment thereof of claim 1, wherein the light chain variable region comprises SEQ ID NO:2.

11. The monoclonal antibody or the fragment thereof of claim 1, wherein the heavy chain variable region comprises SEQ ID NO:1.

* * * * *

UNITED STATES PATENT AND TRADEMARK OFFICE
CERTIFICATE OF CORRECTION

PATENT NO. : 12,365,739 B2
APPLICATION NO. : 17/702890
DATED : July 22, 2025
INVENTOR(S) : Ferrario et al.

Page 1 of 1

It is certified that error appears in the above-identified patent and that said Letters Patent is hereby corrected as shown below:

In the Specification

Column 3, Line 40: Please correct "$5 \times 10^{-1}$" to read --$5 \times 10^{-7}$--

Column 14, Line 20: Please correct "(LC CDR3))." to read --(LC CDR3).--

Column 14, Line 46: Please correct "(HC CDR3))." to read --(HC CDR3).--

Column 14, Line 50: Please correct "(HC CDR3))." to read --(HC CDR3).--

Column 19, Line 13: Please correct "(1989));" to read --(1989);--

Column 32, Line 12: Please correct "(ASO), 15, 18, 50" to read --(ASO), $^{15, 18, 50}$--

Column 38, Line 23: Please correct ">99%" to read --$\geq$99%--

Signed and Sealed this
Ninth Day of December, 2025

John A. Squires
*Director of the United States Patent and Trademark Office*

SEQUENCE LISTING

<160> NUMBER OF SEQ ID NOS: 28

<210> SEQ ID NO 1
<211> LENGTH: 11
<212> TYPE: PRT
<213> ORGANISM: Artificial Sequence
<220> FEATURE:
<223> OTHER INFORMATION: VDJ junction region

<400> SEQUENCE: 1

Cys Ala Arg Gly Ser Tyr Tyr Phe Asp Tyr Trp
1               5                   10

<210> SEQ ID NO 2
<211> LENGTH: 10
<212> TYPE: PRT
<213> ORGANISM: Artificial Sequence
<220> FEATURE:
<223> OTHER INFORMATION: VDJ junction region

<400> SEQUENCE: 2

Cys Lys Gln Ser Tyr Asn Leu Arg Thr Phe
1               5                   10

<210> SEQ ID NO 3
<211> LENGTH: 17
<212> TYPE: PRT
<213> ORGANISM: Artificial Sequence
<220> FEATURE:
<223> OTHER INFORMATION: LC CDR1

<400> SEQUENCE: 3

Lys Ser Ser Gln Ser Leu Leu Asn Ser Arg Thr Arg Lys Asn Tyr Leu
1               5                   10                  15

Ala

<210> SEQ ID NO 4
<211> LENGTH: 7
<212> TYPE: PRT
<213> ORGANISM: Artificial Sequence
<220> FEATURE:
<223> OTHER INFORMATION: LC CDR2

<400> SEQUENCE: 4

Trp Ala Ser Thr Arg Glu Ser
1               5

<210> SEQ ID NO 5
<211> LENGTH: 8
<212> TYPE: PRT
<213> ORGANISM: Artificial Sequence
<220> FEATURE:
<223> OTHER INFORMATION: LC CDR3

<400> SEQUENCE: 5

Lys Gln Ser Tyr Asn Leu Arg Thr
1               5

<210> SEQ ID NO 6
<211> LENGTH: 6
<212> TYPE: PRT
<213> ORGANISM: Artificial Sequence
<220> FEATURE:
<223> OTHER INFORMATION: HC CDR1

<400> SEQUENCE: 6

Ser Asp Phe Ala Trp Asn
1               5

<210> SEQ ID NO 7
<211> LENGTH: 16
<212> TYPE: PRT
<213> ORGANISM: Artificial Sequence
<220> FEATURE:
<223> OTHER INFORMATION: LC CDR2

<400> SEQUENCE: 7

Tyr Ile Ser Tyr Ser Gly Asn Thr Tyr Tyr Asn Pro Ser Leu Lys Ser
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: LC CDR3

<400> SEQUENCE: 8

Gly Ser Tyr Tyr Phe Asp Tyr
1               5

<210> SEQ ID NO 9
<211> LENGTH: 12
<212> TYPE: PRT
<213> ORGANISM: Homo sapiens

<400> SEQUENCE: 9

Asp Arg Val Tyr Ile His Pro Phe His Leu Val Ile
1               5                   10

<210> SEQ ID NO 10
<211> LENGTH: 134
<212> TYPE: PRT
<213> ORGANISM: Artificial Sequence
<220> FEATURE:
<223> OTHER INFORMATION: HC variable region

<400> SEQUENCE: 10

Met Arg Val Leu Ile Leu Leu Trp Leu Phe Thr Ala Phe Pro Gly Ile
1               5                   10                  15

Leu Ser Asp Val Gln Leu Gln Glu Ser Gly Pro Gly Leu Val Lys Pro
                20                  25                  30

Ser Gln Ser Leu Ser Leu Thr Cys Thr Val Asn Gly Tyr Ser Ile Thr
            35                  40                  45

Ser Asp Phe Ala Trp Asn Trp Ile Arg Gln Phe Pro Gly Asn Lys Leu
        50                  55                  60

Glu Trp Met Gly Tyr Ile Ser Tyr Ser Gly Asn Thr Tyr Tyr Asn Pro
65                  70                  75                  80

Ser Leu Lys Ser Arg Ile Ser Ile Thr Arg Asp Thr Ser Lys Asn Gln
                85                  90                  95

Phe Phe Leu Gln Leu Asn Ser Val Thr Thr Glu Asp Thr Ala Thr Tyr
            100                 105                 110

Tyr Cys Ala Arg Gly Ser Tyr Tyr Phe Asp Tyr Trp Gly Gln Gly Thr
        115                 120                 125

Thr Leu Thr Val Ser Ser
    130

<210> SEQ ID NO 11

```
<211> LENGTH: 132
<212> TYPE: PRT
<213> ORGANISM: Artificial Sequence
<220> FEATURE:
<223> OTHER INFORMATION: LC variable region

<400> SEQUENCE: 11

Met Asp Ser Gln Ala Gln Val Leu Ile Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Ala Gly Glu Lys Val Thr Met Ser Cys Lys Ser Ser Gln Ser
        35                  40                  45

Leu Leu Asn Ser Arg Thr Arg Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Lys Gln Ser Tyr Asn Leu Arg Thr Phe Gly Gly Gly Thr Lys
        115                 120                 125

Leu Glu Ile Lys
    130

<210> SEQ ID NO 12
<211> LENGTH: 33
<212> TYPE: PRT
<213> ORGANISM: Artificial Sequence
<220> FEATURE:
<223> OTHER INFORMATION: synthesized nucleic acid

<400> SEQUENCE: 12

Thr Gly Thr Gly Cys Ala Ala Gly Ala Gly Gly Ala Thr Cys Cys Thr
1               5                   10                  15

Ala Cys Thr Ala Cys Thr Thr Thr Gly Ala Cys Thr Ala Cys Thr Gly
            20                  25                  30

Gly

<210> SEQ ID NO 13
<211> LENGTH: 30
<212> TYPE: DNA
<213> ORGANISM: Artificial Sequence
<220> FEATURE:
<223> OTHER INFORMATION: synthesized nucleic acid

<400> SEQUENCE: 13
tgcaagcaat cttataatct tcggacgttc                                   30

<210> SEQ ID NO 14
<211> LENGTH: 51
<212> TYPE: DNA
<213> ORGANISM: Artificial Sequence
<220> FEATURE:
<223> OTHER INFORMATION: synthesized nucleic acid LC CDR1

<400> SEQUENCE: 14
aaatccagtc agagtctgct caacagtaga acccgaaaga actacttggc t           51

<210> SEQ ID NO 15
```

```
<211> LENGTH: 21
<212> TYPE: DNA
<213> ORGANISM: Artificial Sequence
<220> FEATURE:
<223> OTHER INFORMATION: synthesized nucleic acid LC CDR2

<400> SEQUENCE: 15
tgggcatcca ctagggaatc t                                           21

<210> SEQ ID NO 16
<211> LENGTH: 24
<212> TYPE: DNA
<213> ORGANISM: Artificial Sequence
<220> FEATURE:
<223> OTHER INFORMATION: synthesized nucleic acid LC CDR3

<400> SEQUENCE: 16
aagcaatctt ataatcttcg gacg                                        24

<210> SEQ ID NO 17
<211> LENGTH: 18
<212> TYPE: DNA
<213> ORGANISM: Artificial Sequence
<220> FEATURE:
<223> OTHER INFORMATION: synthesized nucleic acid HC CDR1

<400> SEQUENCE: 17
agtgattttg cctggaac                                               18

<210> SEQ ID NO 18
<211> LENGTH: 48
<212> TYPE: DNA
<213> ORGANISM: Artificial Sequence
<220> FEATURE:
<223> OTHER INFORMATION: synthesized nucleic acid HC CDR2

<400> SEQUENCE: 18
tacataagct acagtggtaa cacttactac aacccatctc tcaaaagt              48

<210> SEQ ID NO 19
<211> LENGTH: 21
<212> TYPE: DNA
<213> ORGANISM: Artificial Sequence
<220> FEATURE:
<223> OTHER INFORMATION: synthesized nucleic acid HC CDR3

<400> SEQUENCE: 19
ggatcctact actttgacta c                                           21

<210> SEQ ID NO 20
<211> LENGTH: 10
<212> TYPE: PRT
<213> ORGANISM: Homo sapiens

<400> SEQUENCE: 20

Asp Arg Val Tyr Ile His Pro Phe His Leu
1               5                   10

<210> SEQ ID NO 21
<211> LENGTH: 8
<212> TYPE: PRT
<213> ORGANISM: Homo sapiens

<400> SEQUENCE: 21

Asp Arg Val Tyr Ile His Pro Phe
1               5
```

<210> SEQ ID NO 22
<211> LENGTH: 7
<212> TYPE: PRT
<213> ORGANISM: Homo sapiens

<400> SEQUENCE: 22

Asp Arg Val Tyr Ile His Pro
1               5

<210> SEQ ID NO 23
<211> LENGTH: 9
<212> TYPE: PRT
<213> ORGANISM: Homo sapiens

<400> SEQUENCE: 23

Asp Arg Val Tyr Ile His Pro Phe His
1               5

<210> SEQ ID NO 24
<211> LENGTH: 12
<212> TYPE: PRT
<213> ORGANISM: Rattus norvegicus

<400> SEQUENCE: 24

Asp Arg Val Tyr Ile His Pro Phe His Leu Leu Tyr
1               5                   10

<210> SEQ ID NO 25
<211> LENGTH: 402
<212> TYPE: DNA
<213> ORGANISM: Artificial Sequence
<220> FEATURE:
<223> OTHER INFORMATION: HC DNA sequence

<400> SEQUENCE: 25
atgagagtgc tgattctttt gtggctgttc acagcctttc ctggtatcct gtctgatgtg      60
cagcttcagg agtcgggacc tggcctggtg aaaccctctc agtctctgtc cctcacctgc     120
actgtcaacg gctactcaat caccagtgat tttgcctgga actggatccg gcagttccca     180
ggaaacaaac tggagtggat gggctacata agctacagtg taacactta ctacaaccca      240 tctctcaaaa gtcgaatctc tatcactcga gacacatcca agaaccagtt cttcctgcag     300
ttgaattctg tgactactga ggacacagcc acatattact gtgcaagagg atcctactac     360
tttgactact ggggccaagg caccactctc acagtctcct ca                       402

<210> SEQ ID NO 26
<211> LENGTH: 134
<212> TYPE: PRT
<213> ORGANISM: Artificial Sequence
<220> FEATURE:
<223> OTHER INFORMATION: HC amino acid sequence

<400> SEQUENCE: 26

Met Arg Val Leu Ile Leu Leu Trp Leu Phe Thr Ala Phe Pro Gly Ile
1               5                   10                  15

Leu Ser Asp Val Gln Leu Gln Glu Ser Gly Pro Gly Leu Val Lys Pro
            20                  25                  30

Ser Gln Ser Leu Ser Leu Thr Cys Thr Val Asn Gly Tyr Ser Ile Thr
        35                  40                  45

Ser Asp Phe Ala Trp Asn Trp Ile Arg Gln Phe Pro Gly Asn Lys Leu
    50                  55                  60

```
Glu Trp Met Gly Tyr Ile Ser Tyr Ser Gly Asn Thr Tyr Tyr Asn Pro
 65                  70                  75                  80

Ser Leu Lys Ser Arg Ile Ser Ile Thr Arg Asp Thr Ser Lys Asn Gln
                 85                  90                  95

Phe Phe Leu Gln Leu Asn Ser Val Thr Thr Glu Asp Thr Ala Thr Tyr
            100                 105                 110

Tyr Cys Ala Arg Gly Ser Tyr Tyr Phe Asp Tyr Trp Gly Gln Gly Thr
        115                 120                 125

Thr Leu Thr Val Ser Ser
    130
```

<210> SEQ ID NO 27
<211> LENGTH: 396
<212> TYPE: DNA
<213> ORGANISM: Artificial Sequence
<220> FEATURE:
<223> OTHER INFORMATION: LC DNA sequence

<400> SEQUENCE: 27

```
atggattcac aggcccaggt tcttatattg ctgctgctat gggtatctgg tacctgtggg   60
gacattgtga tgtcacagtc tccatcctcc ctggctgtgt cagcaggaga gaaggtcact  120
atgagctgca aatccagtca gagtctgctc aacagtagaa cccgaaagaa ctacttggct  180
tggtaccagc agaaaccagg gcagtctcct aaactgctga tctactgggc atccactagg  240
gaatctgggg tccctgatcg cttcacaggc agtggatctg ggacagattt cactctcacc  300
atcagcagtg tgcaggctga agacctggca gtttattact gcaagcaatc ttataatctt  360
cggacgttcg gtggaggcac caagttggaa atcaaa                            396
```

<210> SEQ ID NO 28
<211> LENGTH: 132
<212> TYPE: PRT
<213> ORGANISM: Artificial Sequence
<220> FEATURE:
<223> OTHER INFORMATION: LC amino acid sequence

<400> SEQUENCE: 28

```
Met Asp Ser Gln Ala Gln Val Leu Ile Leu Leu Leu Leu Trp Val Ser
 1               5                  10                  15

Gly Thr Cys Gly Asp Ile Val Met Ser Gln Ser Pro Ser Ser Leu Ala
                 20                  25                  30

Val Ser Ala Gly Glu Lys Val Thr Met Ser Cys Lys Ser Ser Gln Ser
             35                  40                  45

Leu Leu Asn Ser Arg Thr Arg Lys Asn Tyr Leu Ala Trp Tyr Gln Gln
         50                  55                  60

Lys Pro Gly Gln Ser Pro Lys Leu Leu Ile Tyr Trp Ala Ser Thr Arg
 65                  70                  75                  80

Glu Ser Gly Val Pro Asp Arg Phe Thr Gly Ser Gly Ser Gly Thr Asp
                 85                  90                  95

Phe Thr Leu Thr Ile Ser Ser Val Gln Ala Glu Asp Leu Ala Val Tyr
            100                 105                 110

Tyr Cys Lys Gln Ser Tyr Asn Leu Arg Thr Phe Gly Gly Gly Thr Lys
        115                 120                 125

Leu Glu Ile Lys
    130
```